US011077199B2

(12) United States Patent
Moynihan et al.

(10) Patent No.: US 11,077,199 B2
(45) Date of Patent: Aug. 3, 2021

(54) ALBUMIN BINDING PEPTIDE CONJUGATES AND METHODS THEREOF

(71) Applicant: Massachusetts Institute of Technology, Cambridge, MA (US)

(72) Inventors: Kelly Dare Moynihan, Allston, MA (US); Rebecca Lynn Holden, Cambridge, MA (US); Darrell J. Irvine, Arlington, MA (US); Bradley Lether Pentelute, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/059,523

(22) Filed: Aug. 9, 2018

(65) Prior Publication Data

US 2019/0046654 A1    Feb. 14, 2019

Related U.S. Application Data

(60) Provisional application No. 62/543,163, filed on Aug. 9, 2017.

(51) Int. Cl.
| | | |
|---|---|---|
| *A61K 47/00* | (2006.01) | |
| *A61K 47/64* | (2017.01) | |
| *C07K 14/76* | (2006.01) | |
| *A61P 35/00* | (2006.01) | |
| *C07K 7/08* | (2006.01) | |
| *A61P 31/00* | (2006.01) | |
| *C07K 7/06* | (2006.01) | |
| *A61K 39/00* | (2006.01) | |
| *C07K 14/47* | (2006.01) | |
| *A61K 38/00* | (2006.01) | |

(52) U.S. Cl.
CPC ........ *A61K 47/646* (2017.08); *A61K 39/0011* (2013.01); *A61K 39/001192* (2018.08); *A61P 31/00* (2018.01); *A61P 35/00* (2018.01); *C07K 7/06* (2013.01); *C07K 7/08* (2013.01); *C07K 14/4748* (2013.01); *C07K 14/76* (2013.01); *A61K 38/00* (2013.01); *A61K 2039/55561* (2013.01); *A61K 2039/6031* (2013.01); *A61K 2039/6093* (2013.01); *A61K 2039/876* (2018.08); *C07K 2319/00* (2013.01)

(58) Field of Classification Search
CPC .......... A61K 47/646; A61K 39/001192; A61K 39/0011; A61K 2039/876; A61K 38/00; A61K 2039/55561; A61K 2039/6031; A61K 2039/6093; A61P 31/00; A61P 35/00; C07K 7/06; C07K 7/08; C07K 14/4748; C07K 14/76; C07K 2319/00
See application file for complete search history.

(56) References Cited

U.S. PATENT DOCUMENTS

| | | | |
|---|---|---|---|
| 8,344,177 B2 | 1/2013 | Neri et al. | |
| 2004/0001827 A1* | 1/2004 | Dennis .................. | C07K 16/32 424/144.1 |
| 2006/0073152 A1 | 4/2006 | Dennis | |
| 2011/0301334 A1 | 12/2011 | Bhakta et al. | |
| 2014/0170142 A1 | 6/2014 | Lubman et al. | |
| 2016/0095936 A1* | 4/2016 | Irvine .................. | A61K 47/645 424/194.1 |
| 2016/0333111 A1 | 11/2016 | Bonvini et al. | |

FOREIGN PATENT DOCUMENTS

| | | |
|---|---|---|
| WO | 2005097202 A2 | 10/2005 |
| WO | 2005117984 A2 | 12/2005 |
| WO | 2007092023 A1 | 8/2007 |
| WO | 2009016043 A2 | 2/2009 |
| WO | 2009089295 A2 | 7/2009 |
| WO | 2012004384 A2 | 1/2012 |
| WO | 2012175740 A1 | 12/2012 |
| WO | 2013043070 A2 | 3/2013 |
| WO | 2013043071 A1 | 3/2013 |
| WO | 2013/151771 A1 | 10/2013 |
| WO | 2013148966 A1 | 10/2013 |
| WO | 2013151771 A1 | 10/2013 |
| WO | 2015026892 A1 | 2/2015 |
| WO | 2015166082 A1 | 11/2015 |
| WO | 2015168643 A2 | 11/2015 |
| WO | 2015177175 A2 | 11/2015 |
| WO | 2015/193417 A1 | 12/2015 |
| WO | 2016025645 A1 | 2/2016 |
| WO | 2016077264 A1 | 5/2016 |
| WO | 2016/197975 A1 | 12/2016 |
| WO | 2019032827 A1 | 2/2019 |

OTHER PUBLICATIONS

Chen et al. Fusion Protein Linkers: Property, Design and Functionality. 2013. Adv Drug Deliv Rev. Oct. 15, 2013; 65(10): 1357-1369. (Year: 2013).*
International Search Report and Written Opinion, PCT/US2018/046011, dated Nov. 19, 2018, 15 pages.
Davies-Venn, C. A., et al. "Albumin-Binding domain Conjugate for Near-Infrared Fluorescence Lymphatic Imaging," Molecular Imaging and Biology, vol. 14: 301-314 (2012).
Dennis, M. S. et al., "Albumin Binding as a General Strategy for Improving the Pharmacokinetics of Proteins," Journal of Biological Chemistry, vol. 277: 35035-35043 (2002).

(Continued)

*Primary Examiner* — James H Alstrum-Acevedo
*Assistant Examiner* — Mercy H Sabila
(74) *Attorney, Agent, or Firm* — Nelson Mullins Riley & Scarborough LLP

(57) ABSTRACT

The present invention provides a conjugate comprising an albumin binding peptide and a cargo, compositions for directing cargos to the lymphatic system, and vaccines. The methods of the invention can be used to increase an immune response, or to treat cancer or an infectious disease.

24 Claims, 6 Drawing Sheets

Specification includes a Sequence Listing.

(56) References Cited

OTHER PUBLICATIONS

Hacohen, N., et al., "Getting personal with neoantigen-based therapeutic cancer vaccines," Cancer Immunol Res., vol. 1:11-15 (2013).
International Preliminary Report on Patentabilty, PCT/US2018/046011, dated Feb. 11, 2020, 7 pages.
Levy, O. E. et al., "Novel Exenatide Analogs with Peptidic Albumin Binding Domains: Potent Anti-Diabetic Agents with Extended Duration of Action," PLoS ONE, vol. 9(2) e87704, 9 pages (2014).
Liu, H. et al., "Structure-based programming of lymph node targeting in molecular vaccines," Nature, vol. 507:519-522 (2014).
Ma, Y. et al., "A novel recombinant slow-release TNF alpha-derived peptide effectively inhibits tumor growth and angiogenesis," Scientific Reports, vol. 5:13595 17 pages (2015).
Melief, C. J. M. et al., "Immunotherapy of established (pre)malignant disease by synthetic long peptide vaccines," Nat Rev Cancer, vol. 8:351-360 (2008).
Mijalis, A. J. et al., "A fully automated flow-based approach for accelerated peptide synthesis.," Nat Chem Biol., vol. 13: 464-466 (2017).
Schwartzentruber, D. J. et al., "gp100 Peptide Vaccine and Interleukin-2 in Patients with Advanced Melanoma," New England Journal of Medicine, vol. 364: 2119-2127 (2011).
Van Stipdonk, M. J. B. et al., "Design of agonistic altered peptides for the robust induction of CTL directed towards H-2Dbeta in complex with the melanoma-associated epitope gp100," Cancer Research, vol. 69:7784-7792 (2009).
Haddad D., et al., "Characterization of antibody responses to a Plasmodium falciparum blood-stage antigen induced by a DNA prime/protein boost immunization protocol.," Scandanavian Journal of Immunology, vol. 49(5): 506-514 (1999).
Power, U. et al., "Induction of Protective Immunity in Rodents by Vaccination with a Prokaryotically Expressed Recombinant Fusion Protein Containing a Respiratory Syncytial Virus G Protein Fragment," Virology, vol. 230(2): 155-166 (1997).
Sjölander A., et al., "Plasmodium falciparum: the immune response in rabbits to the clustered asparagine-rich protein (CARP) after immunization in Freund's adjuvant or immunostimulating complexes (ISCOMs)," Experimental Parasitology, vol. 76(2): 134-145 (1993).
Stork R., "A novel tri-functional antibody fusion protein with improved pharmacokinetic properties generated by fusing a bispecific single-chain diabody with an albumin-binding domain from streptococcal protein G ," Protein engineering, design and selection, vol. 20(11): 569-576 (2007).
Svanholm, C. et al., "Enhancement of antibody responses by DNA immunization using expression vectors mediating efficient antigen secretion," Journal of Immunological Methods, vol. 228(1-2): 121-130 (1999).
Tolmachev V., "Radionuclide therapy of HER2-positive microxenografts using a 177Lu-labeled HER2-specific Affibody molecule," Cancer Research, vol. 67(6): 2773-2782 (2007).

* cited by examiner

SEQUENCE LISTING

```
<160> NUMBER OF SEQ ID NOS: 47

<210> SEQ ID NO 1
<211> LENGTH: 13
<212> TYPE: PRT
<213> ORGANISM: Artificial Sequence
<220> FEATURE:
<223> OTHER INFORMATION: Synthetic: Albumin binding peptide
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(9)
<223> OTHER INFORMATION: Xaa can be any naturally occurring amino acid
```

-continued

```
<220> FEATURE:
<221> NAME/KEY: misc_feature
<222> LOCATION: (11)..(13)
<223> OTHER INFORMATION: Xaa can be any naturally occurring amino acid

<400> SEQUENCE: 1

Xaa Xaa Xaa Cys Xaa Xaa Xaa Xaa Xaa Cys Xaa Xaa Xaa
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic: Albumin binding peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 2

Xaa Phe Cys Xaa Asp Trp Pro Xaa Xaa Xaa Ser Cys Xaa
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic: Albumin binding peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 3

Xaa Val Cys Tyr Xaa Xaa Xaa Ile Cys Phe Xaa
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic: Albumin binding peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa is Ile, Phe, Tyr or Val
```

```
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 4

Xaa Cys Tyr Xaa Pro Gly Xaa Cys Xaa
1               5

<210> SEQ ID NO 5
<211> LENGTH: 13
<212> TYPE: PRT
<213> ORGANISM: Artificial Sequence
<220> FEATURE:
<223> OTHER INFORMATION: Synthetic: Albumin binding peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 5

Xaa Asp Xaa Cys Leu Pro Xaa Trp Gly Cys Leu Trp Xaa
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic: Albumin binding peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 6

Xaa Trp Cys Asp Xaa Xaa Leu Xaa Ala Xaa Asp Leu Cys Xaa
1               5                   10

<210> SEQ ID NO 7
<211> LENGTH: 12
```

```
<212> TYPE: PRT
<213> ORGANISM: Artificial Sequence
<220> FEATURE:
<223> OTHER INFORMATION: Synthetic: Albumin binding peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 7

Xaa Asp Leu Val Xaa Leu Gly Leu Glu Cys Trp Xaa
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic: Albumin binding peptide

<400> SEQUENCE: 8

Asp Leu Cys Leu Arg Asp Trp Gly Cys Leu Trp
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic: Albumin binding peptide

<400> SEQUENCE: 9

Asp Ile Cys Leu Pro Arg Trp Gly Cys Leu Trp
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Synthetic: Albumin binding peptide

<400> SEQUENCE: 10

Met Glu Asp Ile Cys Leu Pro Arg Trp Gly Cys Leu Trp Gly Asp
1               5                   10                  15

<210> SEQ ID NO 11
<211> LENGTH: 20
<212> TYPE: PRT
<213> ORGANISM: Artificial Sequence
<220> FEATURE:
<223> OTHER INFORMATION: Synthetic: Albumin binding peptide

<400> SEQUENCE: 11

Gln Arg Leu Met Glu Asp Ile Cys Leu Pro Arg Trp Gly Cys Leu Trp
1               5                   10                  15
Glu Asp Asp Glu
            20

<210> SEQ ID NO 12
```

```
<211> LENGTH: 20
<212> TYPE: PRT
<213> ORGANISM: Artificial Sequence
<220> FEATURE:
<223> OTHER INFORMATION: Synthetic: Albumin binding peptide

<400> SEQUENCE: 12

Gln Gly Leu Ile Gly Asp Ile Cys Leu Pro Arg Trp Gly Cys Leu Trp
1               5                   10                  15

Gly Arg Ser Val
            20

<210> SEQ ID NO 13
<211> LENGTH: 21
<212> TYPE: PRT
<213> ORGANISM: Artificial Sequence
<220> FEATURE:
<223> OTHER INFORMATION: Synthetic: Albumin binding peptide

<400> SEQUENCE: 13

Gln Gly Leu Ile Gly Asp Ile Cys Leu Pro Arg Trp Gly Cys Leu Trp
1               5                   10                  15

Gly Arg Ser Val Lys
            20

<210> SEQ ID NO 14
<211> LENGTH: 15
<212> TYPE: PRT
<213> ORGANISM: Artificial Sequence
<220> FEATURE:
<223> OTHER INFORMATION: Synthetic: Albumin binding peptide

<400> SEQUENCE: 14

Glu Asp Ile Cys Leu Pro Arg Trp Gly Cys Leu Trp Glu Asp Asp
1               5                   10                  15

<210> SEQ ID NO 15
<211> LENGTH: 18
<212> TYPE: PRT
<213> ORGANISM: Artificial Sequence
<220> FEATURE:
<223> OTHER INFORMATION: Synthetic: Albumin binding peptide

<400> SEQUENCE: 15

Arg Leu Met Glu Asp Ile Cys Leu Pro Arg Trp Gly Cys Leu Trp Glu
1               5                   10                  15

Asp Asp

<210> SEQ ID NO 16
<211> LENGTH: 16
<212> TYPE: PRT
<213> ORGANISM: Artificial Sequence
<220> FEATURE:
<223> OTHER INFORMATION: Synthetic: Albumin binding peptide

<400> SEQUENCE: 16

Met Glu Asp Ile Cys Leu Pro Arg Trp Gly Cys Leu Trp Glu Asp Asp
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic: Albumin binding peptide
```

```
<400> SEQUENCE: 17

Met Glu Asp Ile Cys Leu Pro Arg Trp Gly Cys Leu Trp Glu Asp
1               5                   10                  15

<210> SEQ ID NO 18
<211> LENGTH: 18
<212> TYPE: PRT
<213> ORGANISM: Artificial Sequence
<220> FEATURE:
<223> OTHER INFORMATION: Synthetic: Albumin binding peptide

<400> SEQUENCE: 18

Arg Leu Met Glu Asp Ile Cys Leu Ala Arg Trp Gly Cys Leu Trp Glu
1               5                   10                  15

Asp Asp

<210> SEQ ID NO 19
<211> LENGTH: 20
<212> TYPE: PRT
<213> ORGANISM: Artificial Sequence
<220> FEATURE:
<223> OTHER INFORMATION: Synthetic: Albumin binding peptide

<400> SEQUENCE: 19

Glu Val Arg Ser Phe Cys Thr Arg Trp Pro Ala Glu Lys Ser Cys Lys
1               5                   10                  15

Pro Leu Arg Gly
            20

<210> SEQ ID NO 20
<211> LENGTH: 20
<212> TYPE: PRT
<213> ORGANISM: Artificial Sequence
<220> FEATURE:
<223> OTHER INFORMATION: Synthetic: Albumin binding peptide

<400> SEQUENCE: 20

Arg Ala Pro Glu Ser Phe Val Cys Tyr Trp Glu Thr Ile Cys Phe Glu
1               5                   10                  15

Arg Ser Glu Gln
            20

<210> SEQ ID NO 21
<211> LENGTH: 11
<212> TYPE: PRT
<213> ORGANISM: Artificial Sequence
<220> FEATURE:
<223> OTHER INFORMATION: Synthetic: Albumin binding peptide

<400> SEQUENCE: 21

Glu Met Cys Tyr Phe Pro Gly Ile Cys Trp Met
1               5                   10

<210> SEQ ID NO 22
<211> LENGTH: 21
<212> TYPE: PRT
<213> ORGANISM: Artificial Sequence
<220> FEATURE:
<223> OTHER INFORMATION: Synthetic: Albumin binding peptide
<220> FEATURE:
<221> NAME/KEY: misc_feature
<222> LOCATION: (1)..(5)
<223> OTHER INFORMATION: Xaa can be any naturally occurring amino acid;
      one Xaa may be present or absent
<220> FEATURE:
<221> NAME/KEY: misc_feature
```

```
<222> LOCATION: (7)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (17)..(21)
<223> OTHER INFORMATION: Xaa can be any naturally occurring amino acid;
      one Xaa may be present or absent

<400> SEQUENCE: 22

Xaa Xaa Xaa Xaa Xaa Asp Xaa Cys Leu Pro Xaa Trp Gly Cys Leu Trp
1               5                   10                  15

Xaa Xaa Xaa Xaa Xaa
            20

<210> SEQ ID NO 23
<211> LENGTH: 21
<212> TYPE: PRT
<213> ORGANISM: Artificial Sequence
<220> FEATURE:
<223> OTHER INFORMATION: Synthetic: Albumin binding peptide
<220> FEATURE:
<221> NAME/KEY: misc_feature
<222> LOCATION: (1)..(5)
<223> OTHER INFORMATION: Xaa can be any naturally occurring amino acid;
      one Xaa may be present or absent
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid
<220> FEATURE:
<221> NAME/KEY: misc_feature
<222> LOCATION: (17)..(21)
<223> OTHER INFORMATION: Xaa can be any naturally occurring amino acid;
      one Xaa may be present or absent

<400> SEQUENCE: 23

Xaa Xaa Xaa Xaa Xaa Phe Cys Xaa Asp Trp Pro Xaa Xaa Xaa Ser Cys
1               5                   10                  15

Xaa Xaa Xaa Xaa Xaa
            20

<210> SEQ ID NO 24
<211> LENGTH: 19
<212> TYPE: PRT
<213> ORGANISM: Artificial Sequence
<220> FEATURE:
<223> OTHER INFORMATION: Synthetic: Albumin binding peptide
<220> FEATURE:
<221> NAME/KEY: misc_feature
<222> LOCATION: (1)..(5)
<223> OTHER INFORMATION: Xaa can be any naturally occurring amino acid;
      one Xaa may be present or absent
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (15)..(19)
<223> OTHER INFORMATION: Xaa can be any naturally occurring amino acid;
      one Xaa may be present or absent

<400> SEQUENCE: 24

Xaa Xaa Xaa Xaa Xaa Val Cys Tyr Xaa Xaa Xaa Ile Cys Phe Xaa Xaa
```

```
1               5                   10                  15

Xaa Xaa Xaa

<210> SEQ ID NO 25
<211> LENGTH: 18
<212> TYPE: PRT
<213> ORGANISM: Artificial Sequence
<220> FEATURE:
<223> OTHER INFORMATION: Synthetic: Albumin binding peptide
<220> FEATURE:
<221> NAME/KEY: misc_feature
<222> LOCATION: (1)..(5)
<223> OTHER INFORMATION: Xaa can be any naturally occurring amino acid;
      one Xaa may be present or absent
<220> FEATURE:
<221> NAME/KEY: misc_feature
<222> LOCATION: (8)..(8)
<223> OTHER INFORMATION: Xaa is Ile, Phe, Tyr or Val
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(18)
<223> OTHER INFORMATION: Xaa can be any naturally occurring amino acid;
      one Xaa may be present or absent

<400> SEQUENCE: 25

Xaa Xaa Xaa Xaa Xaa Cys Tyr Xaa Pro Gly Xaa Cys Xaa Xaa Xaa Xaa
1               5                   10                  15

Xaa Xaa

<210> SEQ ID NO 26
<211> LENGTH: 11
<212> TYPE: PRT
<213> ORGANISM: Artificial Sequence
<220> FEATURE:
<223> OTHER INFORMATION: Synthetic: Albumin binding peptide

<400> SEQUENCE: 26

Asp Leu Cys Leu Arg Asp Trp Gly Cys Leu Trp
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic: Albumin binding peptide

<400> SEQUENCE: 27

Asp Ile Cys Leu Pro Arg Trp Gly Cys Leu Trp
1               5                   10

<210> SEQ ID NO 28
<211> LENGTH: 15
<212> TYPE: PRT
<213> ORGANISM: Artificial Sequence
<220> FEATURE:
<223> OTHER INFORMATION: Synthetic: Albumin binding peptide

<400> SEQUENCE: 28

Met Glu Asp Ile Cys Leu Pro Arg Trp Gly Cys Leu Trp Glu Asp
1               5                   10                  15

<210> SEQ ID NO 29
<211> LENGTH: 20
```

```
<212> TYPE: PRT
<213> ORGANISM: Artificial Sequence
<220> FEATURE:
<223> OTHER INFORMATION: Synthetic: Albumin binding peptide

<400> SEQUENCE: 29

Gln Arg Leu Met Glu Asp Ile Cys Leu Pro Arg Trp Gly Cys Leu Trp
1               5                   10                  15

Glu Asp Asp Phe
            20

<210> SEQ ID NO 30
<211> LENGTH: 20
<212> TYPE: PRT
<213> ORGANISM: Artificial Sequence
<220> FEATURE:
<223> OTHER INFORMATION: Synthetic: Albumin binding peptide

<400> SEQUENCE: 30

Gln Gly Leu Ile Gly Asp Ile Cys Leu Pro Arg Trp Gly Cys Leu Trp
1               5                   10                  15

Gly Asp Ser Val
            20

<210> SEQ ID NO 31
<211> LENGTH: 21
<212> TYPE: PRT
<213> ORGANISM: Artificial Sequence
<220> FEATURE:
<223> OTHER INFORMATION: Synthetic: Albumin binding peptide

<400> SEQUENCE: 31

Gln Gly Leu Ile Gly Asp Ile Cys Leu Pro Arg Trp Gly Cys Leu Trp
1               5                   10                  15

Gly Asp Ser Val Lys
            20

<210> SEQ ID NO 32
<211> LENGTH: 15
<212> TYPE: PRT
<213> ORGANISM: Artificial Sequence
<220> FEATURE:
<223> OTHER INFORMATION: Synthetic: Albumin binding peptide

<400> SEQUENCE: 32

Glu Asp Ile Cys Leu Pro Arg Trp Gly Cys Leu Trp Glu Asp Asp
1               5                   10                  15

<210> SEQ ID NO 33
<211> LENGTH: 18
<212> TYPE: PRT
<213> ORGANISM: Artificial Sequence
<220> FEATURE:
<223> OTHER INFORMATION: Synthetic: Albumin binding peptide

<400> SEQUENCE: 33

Arg Leu Met Glu Asp Ile Cys Leu Pro Arg Trp Gly Cys Leu Trp Glu
1               5                   10                  15

Asp Asp

<210> SEQ ID NO 34
<211> LENGTH: 16
<212> TYPE: PRT
<213> ORGANISM: Artificial Sequence
<220> FEATURE:
```

```
<223> OTHER INFORMATION: Synthetic: Albumin binding peptide

<400> SEQUENCE: 34

Met Glu Asp Ile Cys Leu Pro Arg Trp Gly Cys Leu Trp Glu Asp Asp
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic: Albumin binding peptide

<400> SEQUENCE: 35

Met Glu Asp Ile Cys Leu Pro Arg Trp Gly Cys Leu Trp Glu Asp
1               5                   10                  15

<210> SEQ ID NO 36
<211> LENGTH: 18
<212> TYPE: PRT
<213> ORGANISM: Artificial Sequence
<220> FEATURE:
<223> OTHER INFORMATION: Synthetic: Albumin binding peptide

<400> SEQUENCE: 36

Arg Leu Met Glu Asp Ile Cys Leu Ala Arg Trp Gly Cys Leu Trp Glu
1               5                   10                  15

Asp Asp

<210> SEQ ID NO 37
<211> LENGTH: 20
<212> TYPE: PRT
<213> ORGANISM: Artificial Sequence
<220> FEATURE:
<223> OTHER INFORMATION: Synthetic: Albumin binding peptide

<400> SEQUENCE: 37

Gln Arg Leu Met Glu Asp Ile Cys Leu Pro Arg Trp Gly Cys Leu Trp
1               5                   10                  15

Glu Asp Asp Phe
            20

<210> SEQ ID NO 38
<211> LENGTH: 50
<212> TYPE: PRT
<213> ORGANISM: Artificial Sequence
<220> FEATURE:
<223> OTHER INFORMATION: Synthetic: linker

<400> SEQUENCE: 38

Leu Glu Ala Glu Ala Ala Ala Lys Glu Ala Ala Lys Glu Ala Ala
1               5                   10                  15

Ala Lys Glu Ala Ala Lys Ala Leu Glu Ala Glu Ala Ala Ala Lys
            20                  25                  30

Glu Ala Ala Ala Lys Glu Ala Ala Ala Lys Glu Ala Ala Ala Lys Ala
                35                  40                  45

Leu Glu
    50

<210> SEQ ID NO 39
<211> LENGTH: 4
<212> TYPE: PRT
<213> ORGANISM: Artificial Sequence
<220> FEATURE:
```

```
<223> OTHER INFORMATION: Synthetic: linker

<400> SEQUENCE: 39

Gly Gly Ser Gly
1

<210> SEQ ID NO 40
<211> LENGTH: 4
<212> TYPE: PRT
<213> ORGANISM: Artificial Sequence
<220> FEATURE:
<223> OTHER INFORMATION: Synthetic: linker

<400> SEQUENCE: 40

Gly Ser Ala Thr
1

<210> SEQ ID NO 41
<211> LENGTH: 20
<212> TYPE: PRT
<213> ORGANISM: Artificial Sequence
<220> FEATURE:
<223> OTHER INFORMATION: Synthetic: EGP long peptide

<400> SEQUENCE: 41

Ala Val Gly Ala Leu Glu Gly Pro Arg Asn Gln Asp Trp Leu Gly Val
1               5                   10                  15

Pro Arg Gln Leu
            20

<210> SEQ ID NO 42
<211> LENGTH: 5
<212> TYPE: PRT
<213> ORGANISM: Artificial Sequence
<220> FEATURE:
<223> OTHER INFORMATION: Synthetic: linker

<400> SEQUENCE: 42

Gly Gly Gly Gly Ser
1               5

<210> SEQ ID NO 43
<211> LENGTH: 36
<212> TYPE: PRT
<213> ORGANISM: Artificial Sequence
<220> FEATURE:
<223> OTHER INFORMATION: Synthetic: ABP-G4S-EGP long

<400> SEQUENCE: 43

Asp Ile Cys Leu Pro Arg Trp Gly Cys Leu Trp Gly Gly Gly Gly Ser
1               5                   10                  15

Ala Val Gly Ala Leu Glu Gly Pro Arg Asn Gln Asp Trp Leu Gly Val
                20                  25                  30

Pro Arg Gln Leu
            35

<210> SEQ ID NO 44
<211> LENGTH: 5
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (1)..(5)
<223> OTHER INFORMATION: "Gly Gly Gly Gly Ser" may repeat indefinitely
```

<400> SEQUENCE: 44

Gly Gly Gly Gly Ser
1               5

<210> SEQ ID NO 45
<211> LENGTH: 27
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (12)..(26)
<223> OTHER INFORMATION: At least 1 and up to 3 repeats of "EAAAK" may
      be present or
      absent

<400> SEQUENCE: 45

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25

<210> SEQ ID NO 46
<211> LENGTH: 20
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (5)..(20)
<223> OTHER INFORMATION: At least one and up to four repeats of "GGSG"
      may be present or absent

<400> SEQUENCE: 46

Gly Gly Ser Gly Gly Gly Ser Gly Gly Gly Ser Gly Gly Gly Ser Gly
1               5                   10                  15

Gly Gly Ser Gly
            20

<210> SEQ ID NO 47
<211> LENGTH: 30
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (7)..(30)
<223> OTHER INFORMATION: At least one and up to four repeats of "GGSGGS"
      may be present or absent

<400> SEQUENCE: 47

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30

ALBUMIN BINDING PEPTIDE CONJUGATES AND METHODS THEREOF

RELATED INFORMATION PARAGRAPH

This application claims the benefit of the priority date of U.S. Provisional Application No. 62/543,163, filed on Aug. 9, 2017, the content of which is hereby incorporated by reference in its entirety.

GOVERNMENT FUNDING

This invention was made with Government support under Grant No. R01 EB022433 awarded by the National Institutes of Health. The Government has certain rights in the invention.

STATEMENT REGARDING SEQUENCE LISTING

The instant application contains a Sequence Listing which has been submitted in ASCII format via EFS-Web and is hereby incorporated by reference in its entirety. Said ASCII copy, created on Oct. 31, 2018, is named "MITN-042_Sequence-Listing.txt" and is 18171 Kilobytes in size. The Sequence Listing is being submitted by EFS Web and is hereby incorporated by reference into the specification.

BACKGROUND

Peptide vaccines for inducing T cell responses have great potential for use against cancers and other diseases, but they are limited in potency (Hacohen, N., Fritsch, E. F., Carter, T. A., Lander, E. S. & Wu, C. J. Getting personal with neoantigen-based therapeutic cancer vaccines. *Cancer Immunol Res* 1, 11-15, doi:10.1158/2326-6066.CIR-13-0022 (2013); Melief, C. J. M. & van der Burg, S. H. Immunotherapy of established (pre)malignant disease by synthetic long peptide vaccines. *Nat Rev Cancer* 8, 351-360 (2008)). One factor that limits the activity of current vaccines is poor targeting to lymph nodes, where immune responses are primed. Enhanced lymph node targeting can be achieved by adding diacyl lipids separated by a PEG spacer to peptide antigens (Liu, H. et al. Structure-based programming of lymph-node targeting in molecular vaccines. *Nature* 507, 519-522, doi:10.1038/nature12978 (2014)). The mechanism of action is thought to involve binding of endogenous albumin upon injection, which allows peptide antigens to "hitchhike" to the draining lymph node, similar to the mechanism of action of sentinel lymph node mapping dyes used clinically (Lindner, V. & Heinle, H. Binding properties of circulating evans blue in rabbits as determined by disc electrophoresis. *Atherosclerosis* 43, 417-422, (1982)). However, there remains a need for improved compositions for enhancing the antigenicity of peptide vaccines.

SUMMARY OF THE INVENTION

The present disclosure is based, at least in part, on the discovery that an albumin binding peptide covalently linked to an immunomodulatory molecule (e.g., a peptide antigen or a molecular adjuvant) may be used to enhance the antigenicity of the immunomodulatory molecule. The present disclosure is also based, at least in part, on the discovery that an albumin binding peptide covalently linked to an immunomodulatory molecule (e.g., a peptide antigen or a molecular adjuvant) may prime an endogenous immune response. In addition, the present disclosure is based, at least in part, on the discovery that an albumin binding peptide covalently linked to an immunomodulatory molecule (e.g., a peptide antigen or a molecular adjuvant) may be used in a method for treating cancer or an infectious disease, or for increasing an immune response in a subject.

Accordingly, in one aspect, the disclosure provides a conjugate comprising an albumin binding peptide and an immunomodulatory molecule, wherein the albumin binding peptide is operatively coupled to the immunomodulatory molecule with or without a linker domain.

In another aspect, the disclosure provides a composition for directing immunomodulatory molecules to the lymphatic system, wherein the composition comprises a conjugate comprising an albumin binding peptide and an immunomodulatory molecule, wherein the albumin binding peptide is operatively coupled to the immunomodulatory molecule with or without a linker domain.

In certain embodiments, the albumin binding peptide is covalently linked to the immunomodulatory molecule.

In certain embodiments, the albumin binding peptide is operatively coupled to the immunomodulatory molecule via a linker domain. In certain embodiments, the linker domain comprises a Gly-Ser linker, such as a $(Gly_4Ser)_n$ linker (SEQ ID NO: 44). In certain embodiments, the linker domain comprises a polyethylene glycol (PEG) linker, such as a $PEG_{2000}$ linker.

In certain embodiments, the immunomodulatory molecule is a peptide antigen or a molecular adjuvant. In certain embodiment, the peptide antigen is a cancer antigen. In certain embodiments, the peptide antigen is a melanoma antigen. In certain embodiments, the molecular adjuvant is CpG DNA.

In certain embodiments, the albumin binding peptide comprises the amino acid sequence DICLPRWGCLW (SEQ ID NO: 9).

In certain embodiments, the invention provides a vaccine comprising a conjugate of the disclosure. In certain embodiments, the vaccine comprises a conjugate of the disclosure and a pharmaceutically acceptable carrier or excipient. In certain embodiments, the vaccine comprises a conjugate of the disclosure and an adjuvant.

In certain embodiments, the conjugate exhibits increased accumulation in the lymph node when administered to the subject in vivo compared to administration of the antigen alone.

In certain embodiments, the invention provides an immunogenic composition comprising a conjugate of the disclosure. In certain embodiments, the invention provides an immunogenic composition comprising a vaccine of the disclosure.

In certain embodiments, the disclosure provides a method for treating cancer or an infectious disease comprising administering to a subject an effective amount of a conjugate of the disclosure to reduce one or more symptoms of the cancer or infectious disease compared to a control.

In certain embodiments, the disclosure provides a method for increasing an immune response in a subject comprising administering to the subject an effective amount of a conjugate of the disclosure to increase the immune response in the subject.

In certain embodiments, a subject has cancer or an infectious disease.

In certain embodiments, the invention provides a nucleic acid molecule encoding a conjugate of the disclosure. In certain embodiments, the invention provides a recombinant expression vector comprising a nucleic acid molecule encoding a conjugate of the disclosure. In certain embodiments, the invention provides a host cell transformed with the recombinant expression vector.

In certain embodiments, the invention provides a method of making a conjugate of the disclosure comprising providing a host cell comprising a nucleic acid sequence that encodes the conjugate, and maintaining the host cell under conditions in which the conjugate is expressed.

DETAILED DESCRIPTION OF THE INVENTION

Figure 1:
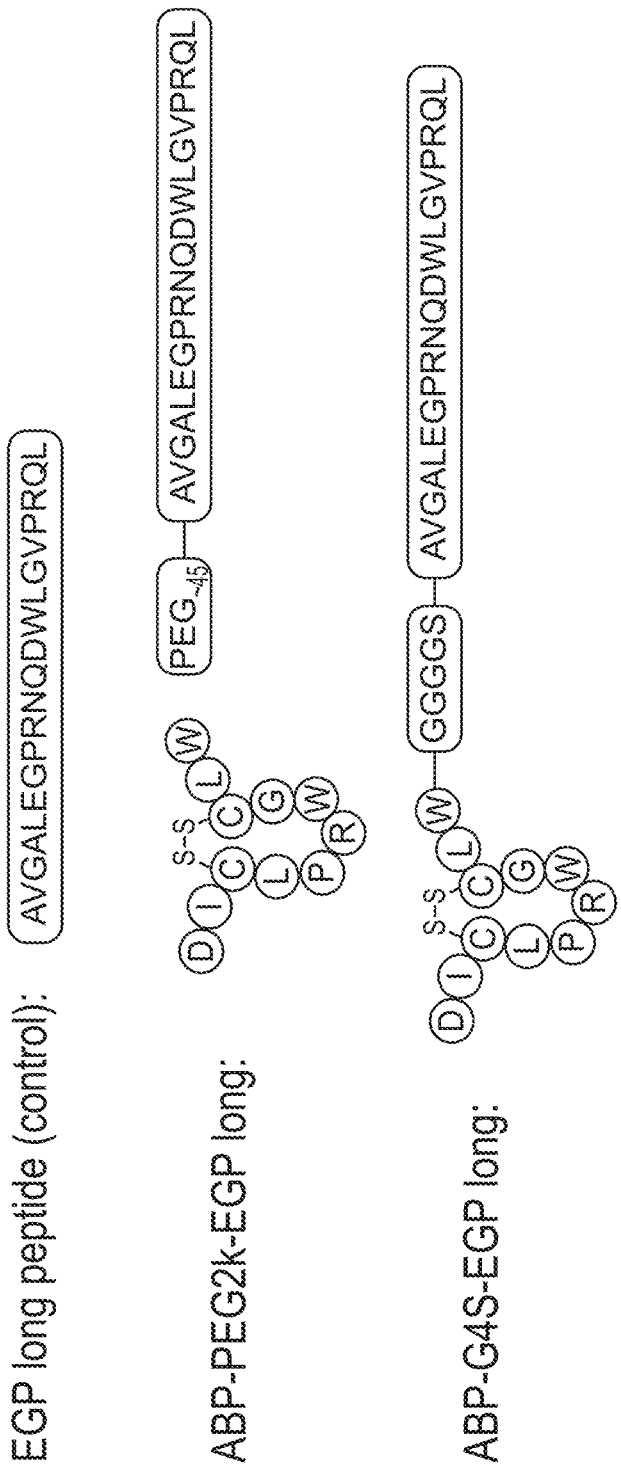
FIG. 1 is a schematic depicting exemplary albumin binding peptide-antigen constructs. ABP-PEG2k-EGP long has the configuration: Albumin binding peptide (cyclized DICLPRWGCLW (SEQ ID NO: 9)) operably coupled via a PEG2k linker to an EGP long peptide (AVGALEGPRNQDWLGVPRQL (SEQ ID NO: 41)). ABP-G4S-EGP long (SEQ ID NO: 43) has the configuration: Albumin binding peptide (cyclized DICLPRWGCLW (SEQ ID NO: 9)) operably coupled via a Gly$_4$Ser linker (SEQ ID NO: 42) to an EGP long peptide (AVGALEGPRNQDWLGVPRQL (SEQ ID NO: 41)).

The present disclosure provides a novel method of enhancing antigenicity of peptide antigens by tethering them to albumin-binding peptides (ABPs).

Prior to the discovery of the present invention, albumin binding peptides remained largely unexplored in the context of vaccinology. They have previously been used to extend the pharmacokinetics of protein therapeutics in several preclinical studies (Dennis, M. S. et al. Albumin Binding as a General Strategy for Improving the Pharmacokinetics of Proteins. *Journal of Biological Chemistry* 277, 35035-35043 (2002); Levy, O. E. et al. Novel Exenatide Analogs with Peptidic Albumin Binding Domains: Potent Anti-Diabetic Agents with Extended Duration of Action. *PLoS ONE* 9, e87704, doi:10.1371/journal.pone.0087704 (2014)).

The present disclosure provides the novel discovery that albumin binding peptides (ABPs) are useful for generating peptide vaccines. ABPs covalently linked to peptide antigens could direct these antigens to the lymphatic system via albumin hitchhiking, a novel application for these under-utilized sequences. They also provide several technical advances over lipidic albumin binders, such as "all on resin" synthesis. Additionally, libraries of albumin-binding peptides have been characterized, which could allow for precise control over albumin-binding affinity, which may be important for the resulting immune response.

The cyclized peptide DICLPRWGCLW (SEQ ID NO: 9) has been identified as the minimal core sequence for achieving binding to serum albumin from multiple species, including mice and humans (Dennis, M. S. et al. Albumin Binding as a General Strategy for Improving the Pharmacokinetics of Proteins. *Journal of Biological Chemistry* 277, 35035-35043 (2002)). This sequence was selected as an albumin-binding peptide and utilized in the experiments described herein.

In some embodiments, the albumin binding peptide conjugates of the disclosure include an albumin binding peptide operatively coupled to a cargo, e.g., an immunomodulatory molecule. In some embodiments, the immunomodulatory molecule is an antigen, such as a peptide antigen, a polypeptide antigen, an antigenic protein. In some embodiments, the immunomodulatory molecule is a molecular adjuvant.

In some embodiments, the disclosure provides albumin binding peptide conjugates for use in immunogenic compositions. In certain embodiments, the albumin binding peptide conjugates effectively target lymph nodes. Albumin binding peptide conjugates may be trafficked from the site of administration through the lymph to the lymph node where they may accumulate and activate immune cells.

Albumin binding peptide conjugates typically include at least two domains: (1) an albumin binding peptide and (2) a cargo (for example, a peptide antigen or a molecular adjuvant). In some embodiments, the albumin binding peptide may be operatively coupled to the cargo via a linker domain. Therefore, in some embodiments, the albumin binding peptide conjugate includes three domains. Accordingly, in some embodiments, the general structure of the conjugate is ABP-C, where "ABP" is an albumin binding peptide and "C" is a cargo such as a peptide antigen or a molecular adjuvant. In some embodiments, the general structure of the conjugate is ABP-L-C, where "ABP" is an albumin binding peptide, "L" is a linker domain, and "C" is a cargo such as a peptide antigen or a molecular adjuvant.

Definitions

Terms used in the claims and specification are defined as set forth below unless otherwise specified.

An "albumin binding peptide conjugate" or "conjugate" refers to an albumin binding peptide (ABP) conjugated to a cargo. In some embodiments, the albumin binding peptide is conjugated to the cargo via a linker domain. In some embodiments, the "cargo" is an immunomodulatory molecule. The terms "albumin binding peptide conjugate" or "conjugate" may be used interchangeably with the terms "albumin binding peptide-antigen constructs" and "albumin binding peptide vaccines."

A "cargo" refers to a an agent that is conjugated to an albumin binding peptide. In some embodiments, the cargo is conjugated to the albumin binding peptide via a linker domain. In some embodiments, the cargo is an immunomodulatory molecule. In some embodiments, the cargo is an antigen. In some embodiments, the cargo is a peptide antigen. In some embodiments, the cargo is a molecular adjuvant. In some embodiments, the cargo is another agent.

An "immunomodulatory molecule" refers to an agent that modulates the immune response (e.g., stimulate, induce, enhance, reduce, or decrease). In some embodiments, the immunomodulatory molecule may be an antigen. For example, in some embodiments, the antigen may be a peptide antigen. In some embodiments, the immunomodulatory molecule may be a molecular adjuvant.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, larger "peptide insertions," can also be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

"Polypeptide," "peptide", and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081, 1991; Ohtsuka et al., Biol. Chem. 260:2605-2608, 1985; and Cassol et al, 1992; Rossolini et al, Mol. Cell. Probes 8:91-98, 1994). For arginine and leucine, modifications at the second base can also be conservative. The term nucleic acid is used interchangeably with gene, cDNA, and mRNA encoded by a gene.

Polynucleotides used herein can be composed of any polyribonucleotide or polydeoxyribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms. Polynucleotides may be synthetic or isolated nucleic acid polymers including a plurality of nucleotide subunits.

As used herein, the terms "linked," "conjugated," "coupled," "fused," or "fusion," are used interchangeably when referring to the joining together of two more elements or components or domains, by whatever means including chemical conjugation or recombinant means. Methods of chemical conjugation (e.g., using heterobifunctional cross-linking agents) are known in the art.

A peptide, polypeptide, or amino acid sequence "derived from" a designated polypeptide or protein refers to the origin of the polypeptide. Preferably, the peptide, polypeptide, or amino acid sequence which is derived from a particular sequence has an amino acid sequence that is essentially identical to that sequence or a portion thereof, wherein the portion consists of at least 5-15 amino acids, at least 10-20 amino acids, at least 20-30 amino acids, at least 30-50 amino acids, or which is otherwise identifiable to one of ordinary skill in the art as having its origin in the sequence. Polypeptides derived from another peptide may have one or more mutations relative to the starting polypeptide, e.g., one or more amino acid residues which have been substituted with another amino acid residue or which has one or more amino acid residue insertions or deletions.

A peptide or polypeptide can comprise an amino acid sequence which is not naturally occurring. Such variants necessarily have less than 100% sequence identity or similarity with the starting molecule. In certain embodiments, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

In certain embodiments, there is one amino acid difference between a starting polypeptide sequence and the sequence derived therefrom. Identity or similarity with respect to this sequence is defined herein as the percentage of amino acid residues in the candidate sequence that are identical (i.e., same residue) with the starting amino acid residues, after aligning the sequences and introducing gaps, if necessary, to achieve the maximum percent sequence identity.

In certain embodiments, the peptides or polypeptides are encoded by a nucleotide sequence. Nucleotide sequences of the invention can be useful for a number of applications, including: cloning, gene therapy, protein expression and purification, mutation introduction, DNA vaccination of a host in need thereof, antibody generation for, e.g., passive immunization, PCR, primer and probe generation, and the like.

The term "ameliorating" refers to any therapeutically beneficial result in the treatment of a disease state, e.g., cancer, including prophylaxis, lessening in the severity or progression, remission, or cure thereof.

The term "in vivo" refers to processes that occur in a living organism.

The term "mammal" or "subject" or "patient" as used herein includes both humans and non-humans and includes, but is not limited to, humans, non-human primates, canines, felines, murines, bovines, equines, and porcines. The terms "mammal," "subject," and "patient" are used interchangeably herein.

The terms "mammal," "subject," and "patient" refer to any individual who is the target of treatment using the compositions of the disclosure. The subject may be a vertebrate, for example, a mammal. The subject may be a human. The subjects may be symptomatic or asymptomatic. The term does not denote a particular age or sex. Adult and newborn subjects, whether male or female, are intended to be covered. A subject may include a control subject or a test subject.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

As used herein, the term "gly-ser polypeptide linker" refers to a peptide that consists of glycine and serine residues. An exemplary gly-ser polypeptide linker comprises the amino acid sequence Ser(Gly$_4$Ser)n. In certain embodiments, n=1. In certain embodiments, n=2. In certain embodiments, n=3, i.e., Ser(Gly$_4$Ser)3. In certain embodiments, n=4, i.e., Ser(Gly$_4$Ser)4. In certain embodiments, n=5. In certain embodiments, n=6. In certain embodiments, n=7. In certain embodiments, n=8. In certain embodiments, n=9. In certain embodiments, n=10. Another exemplary gly-ser polypeptide linker comprises the amino acid sequence (Gly$_4$Ser)n. In certain embodiments, n=1. In certain embodiments, n=2. In certain embodiments, n=3. In certain embodiments, n=4. In certain embodiments, n=5. In certain embodiments, n=6. Another exemplary gly-ser polypeptide linker comprises the amino acid sequence (Gly$_3$Ser)n. certain embodiments, n=1. In certain embodiments, n=2. In certain embodiments, n=3. In certain embodiments, n=4. In certain embodiments, n=5. In certain embodiments, n=6.

A "therapeutic antibody" is an antibody, fragment of an antibody, or construct that is derived from an antibody, and can bind to a cell-surface antigen on a target cell to cause a therapeutic effect. Such antibodies can be chimeric, humanized or fully human antibodies. Methods are known in the art for producing such antibodies. Such antibodies include single chain Fc fragments of antibodies, minibodies and diabodies. Any of the therapeutic antibodies known in the art to be useful for cancer therapy can be used in the combination therapy suitable for use in the methods disclosed herein. Therapeutic antibodies may be monoclonal antibodies or polyclonal antibodies. In preferred embodiments, the therapeutic antibodies target cancer antigens.

As used herein, "cancer antigen" refers to (i) tumor-specific antigens, (ii) tumor-associated antigens, (iii) cells that express tumor-specific antigens, (iv) cells that express tumor-associated antigens, (v) embryonic antigens on tumors, (vi) autologous tumor cells, (vii) tumor-specific membrane antigens, (viii) tumor-associated membrane antigens, (ix) growth factor receptors, (x) growth factor ligands, and (xi) any other type of antigen or antigen-presenting cell or material that is associated with a cancer.

As used herein, we may use the terms "cancer" (or "cancerous"), "hyperproliferative," and "neoplastic" to refer to cells having the capacity for autonomous growth (i.e., an abnormal state or condition characterized by rapidly proliferating cell growth). Hyperproliferative and neoplastic disease states may be categorized as pathologic (i.e., characterizing or constituting a disease state), or they may be categorized as non-pathologic (i.e., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The term "cancer" or "neoplasm" are used to refer to malignancies of the various organ systems, including those affecting the lung, breast, skin (e.g., melanoma), thyroid, lymph glands and lymphoid tissue, gastrointestinal organs, and the genitourinary tract, as well as to adenocarcinomas which are generally considered to include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The albumin binding peptide conjugate can be used to treat patients who have, who are suspected of having, or who may be at high risk for developing any type of cancer, including renal carcinoma or melanoma, or any viral disease. Exemplary carcinomas include those forming from tissue of the cervix, lung, prostate, breast, skin, head and neck, colon and ovary. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

As used herein, "synergy" or "synergistic effect" with regard to an effect produced by two or more individual components refers to a phenomenon in which the total effect produced by these components, when utilized in combination, is greater than the sum of the individual effects of each component acting alone.

The term "sufficient amount" or "amount sufficient to" means an amount sufficient to produce a desired effect. For example, an amount sufficient to reduce the size of a tumor.

The term "effective amount" or "therapeutically effective amount" is a dosage sufficient to provide treatment for a disorder, disease, or condition being treated, to induce or enhance an immune response, to ameliorate a symptom of a disease, or to otherwise provide a desired pharmacologic and/or physiologic effect. A therapeutically effective amount can be a "prophylactically effective amount" as prophylaxis can be considered therapy.

As used herein, "combination therapy" embraces administration of each agent or therapy in a sequential manner in a regimen that will provide beneficial effects of the combination, and co-administration of these agents or therapies in a substantially simultaneous manner, such as in a single capsule having a fixed ratio of these active agents or in multiple, separate capsules for each agent. Combination therapy also includes combinations where individual elements may be administered at different times and/or by different routes but which act in combination to provide a beneficial effect by co-action or pharmacokinetic and pharmacodynamics effect of each agent or tumor treatment approaches of the combination therapy.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

As used herein, "cancer vaccine" refers to a treatment that induces the immune system to attack cells with one or more tumor associated antigens. The vaccine can treat existing cancer (e.g., therapeutic cancer vaccine) or prevent the development of cancer in certain individuals (e.g., prophylactic cancer vaccine). The vaccine creates memory cells that will recognize tumor cells with the antigen and therefore prevent tumor growth. In certain embodiments, the cancer vaccine comprises an immunostimulatory oligonucleotide. In certain embodiments, the cancer vaccine comprises an albumin binding peptide conjugate.

As used herein, an "immunostimulatory oligonucleotide" is an oligonucleotide that can stimulate (e.g., induce or enhance) an immune response.

As used herein, "CG oligodeoxynucleotides (CG ODNs)", also referred to as "CpG ODNs", are short single-stranded synthetic DNA molecules that contain a cytosine nucleotide (C) followed by a guanine nucleotide (G). In certain embodiments, the immunostimulatory oligonucleotide is a CG ODN.

As used herein, "immune cell" is a cell of hematopoietic origin and that plays a role in the immune response. Immune cells include lymphocytes (e.g., B cells and T cells), natural killer cells, and myeloid cells (e.g., monocytes, macrophages, eosinophils, mast cells, basophils, and granulocytes).

The term "T cell" refers to a CD4+ T cell or a CD8+ T cell. The term T cell encompasses TH1 cells, TH2 cells and TH17 cells.

The term "T cell cytoxicity" includes any immune response that is mediated by CD8+ T cell activation. Exemplary immune responses include cytokine production, CD8+ T cell proliferation, granzyme or perforin production, and clearance of an infectious agent.

As generally used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

It must be noted that, as used in the specification and the appended claims, the singular forms "a," "an" and "the" include plural referents unless the context clearly dictates otherwise.

Albumin Binding Peptides

In one aspect, the conjugates of the present invention include an albumin binding peptide (ABP) operatively coupled to a cargo (e.g., an immunomodulatory molecule, such as a peptide antigen or molecular adjuvant). In one embodiment, an albumin binding peptide conjugate may direct the cargo to the lymphatic system via albumin hitchhiking. For example, the albumin binding peptide domain of the conjugate may bind endogenous albumin, which may allow the cargo to "hitchhike" to the draining lymph node. In some embodiments, the present disclosure provides a novel method for enhancing the antigenicity of a cargo (e.g., an immunomodulatory molecule, such as a peptide antigen) by tethering it to an albumin-binding peptide (ABP). In some embodiments, the albumin binding peptide conjugates of the disclosure enhance the antigenicity of a peptide vaccine.

In some embodiments of the disclosure, albumin binding peptides bind a target, preferably a serum protein such as serum albumin, and can be identified in a direct binding assay, or by their ability to compete for target binding with a known ligand for the target. In some embodiments, albumin binding peptides that bind serum albumin include linear and cyclic peptides, such as cyclic peptide compounds comprising the following formulae or are peptides that compete for binding serum albumin of a particular mammalian species with peptides of the following formulae:

```
(Xaa)ₓ-Xaa-Xaa-Cys-Xaa-Xaa-Xaa-Xaa-Xaa-Cys-Xaa-    [SEQ ID NO: 1]

Xaa-(Xaa)_z (Xaa)ₓ-Phe-Cys-Xaa-Asp-Trp-Pro-Xaa-Xaa-Xaa-Ser-    [SEQ ID NO: 2]

Cys-(Xaa)_z (Xaa)ₓ-Val-Cys-Tyr-Xaa-Xaa-Xaa-Ile-Cys-Phe-        [SEQ ID NO: 3]

(Xaa)_z (Xaa)ₓ-Cys-Tyr-Xaa1-Pro-Gly-Xaa-Cys-(Xaa)_z        [SEQ ID NO: 4]
and (Xaa)ₓ-Asp-Xaa-Cys-Leu-Pro-Xaa-Trp-Gly-Cys-Leu-    [SEQ ID NO: 5]

Trp-(Xaa)_z
```

In some embodiments of the disclosure, albumin binding peptide compounds include peptides of the foregoing general formulae wherein Xaa is an amino acid and x and z are a whole number greater or equal to 0 (zero), generally less than 100, preferably less than 10 and more preferably 0, 1, 2, 3, 4 or 5 and more preferably 4 or 5 and wherein Xaa₁ is selected from the group consisting of Be, Phe, Tyr and Val.

Additional albumin binding peptides that bind a serum albumin may be identified as described herein in the context of the following general formulae:

```
(Xaa)ₓ-Trp-Cys-Asp-Xaa-Xaa-Leu-Xaa-Ala-Xaa-Asp-    [SEQ ID NO: 6]

Leu-Cys-(Xaa)_z
and (Xaa)ₓ-Asp-Leu-Val-Xaa-Leu-Gly-Leu-Glu-Cys-Trp-    [SEQ ID NO: 7]

(Xaa)_z
``` where Xaa is an amino acid and x and z are a whole number greater or equal to zero, generally less than 100, preferably less than 10 and more preferably 0, 1, 2, 3, 4 or 5 and more preferably 4 or 5.

In some embodiments of the disclosure, albumin binding peptides include:

| | |
|---|---|
| DLCLRDWGCLW | (SEQ ID NO: 8) |
| DICLPRWGCLW | (SEQ ID NO: 9) |
| MEDICLPRWGCLWGD | (SEQ ID NO: 10) |
| QRLMEDICLPRWGCLWEDDE | (SEQ ID NO: 11) |
| QGLIGDICLPRWGCLWGRSV | (SEQ ID NO: 12) |
| QGLIGDICLPRWGCLWGRSVK | (SEQ ID NO: 13) |
| EDICLPRWGCLWEDD | (SEQ ID NO: 14) |
| RLMEDICLPRWGCLWEDD | (SEQ ID NO: 15) |
| MEDICLPRWGCLWEDD | (SEQ ID NO: 16) |
| MEDICLPRWGCLWED | (SEQ ID NO: 17) |
| RLMEDICLARWGCLWEDD | (SEQ ID NO: 18) |
| EVRSFCTRWPAEKSCKPLRG | (SEQ ID NO: 19) |
| RAPESFVCYWETICFERSEQ | (SEQ ID NO: 20) |
| EMCYFPGICWM | (SEQ ID NO: 21) |

In some embodiments of the disclosure, albumin binding peptides of the present disclosure bind human serum albumin and can be identified by their ability to compete for binding of human serum albumin in an in vitro assay with peptide ligands having the general formulae:

| | |
|---|---|
| Xx D X C L P X W G C L W Xz | (SEQ ID NO: 22) |
| Xx F C X D W P X X X S C Xz | (SEQ ID NO: 23) |
| Xx V C Y X X X I C F Xz | (SEQ ID NO: 24) |
| Xx C Y X₁ P G X C X Xz | (SEQ ID NO: 25) | where Xaa is an amino acid, x and z are preferably 4 or 5, and Xaa₁ is selected from the group consisting of Ile, Phe, Tyr, and Val.

In some embodiments, the albumin binding peptide of the present invention will compete with any of the peptides represented in SEQ ID NO: 8-21 described herein above.

As will be appreciated from the foregoing, the term "compete" and "ability to compete" are relative terms. Thus the terms, when used to describe the albumin binding peptides of the present invention, refer to albumin binding peptides that produce a 50% inhibition of binding of a reference peptide when present at 50 μM, preferably when present at 1 μM, more preferably 100 nM, and preferably when present at 1 nM or less in a standard competition assay as described herein. However, albumin binding peptides having an affinity for a serum albumin of less than about 1 nM and preferably between about 1 pM and 1 nM are equally likely to be albumin binding peptides within the context of the present invention.

For in vitro assay systems to determine whether a peptide or other compound has the "ability" to compete with an albumin binding peptide for binding to serum albumin as noted herein, the skilled artisan can employ any of a number of standard competition assays. Competitive binding assays rely on the ability of a labeled standard to compete with the test sample analyte for binding with a limited amount of ligand. The amount of analyte in the test sample is inversely proportional to the amount of standard that becomes bound to the ligand.

Thus, the skilled artisan may determine whether a peptide or other compound has the ability to compete with an albumin binding peptide for binding to albumin employing procedures that include, but are not limited to, competitive assay systems using techniques such as radioimmunoas says (RIA), enzyme immunoassays (EIA), preferably the enzyme linked immunosorbent assay (ELISA), "sandwich" immunoassays, immunoradiometric assays, fluorescent immunoassays, and immunoelectrophoresis assays, to name but a few.

For these purposes, the selected albumin binding peptide may be labeled with a detectable moiety (the detectably labeled peptide ligand hereafter called the "tracer") and used in a competition assay with a candidate compound for binding albumin. Numerous detectable labels are available that can be preferably grouped into the following categories:

(a) Radioisotopes, such as $^{35}S$, $^{14}C$, $^{125}I$, $^{3}H$, and $^{131}I$. The albumin binding peptide can be labeled with the radioisotope using techniques described in Coligen et al., 1991, eds., Current Protocols in Immunology, Volumes 1 and 2, Wiley-Intersience, New York, N.Y., for example. Radioactivity can be measured using scintillation counting.

(b) Fluorescent labels such as rare earth chelates (europium chelates) or fluorescein and its derivatives, rhodamine and its derivatives, dansyl, lissamine, phycoerythrin, and Texas Red are available. The fluorescent labels can be conjugated to the albumin binding peptide using the techniques disclosed in Current Protocols in Immunology, supra, for example. Fluorescence can be quantified using a fluorimeter.

(c) Various enzyme-substrate labels are available and U.S. Pat. No. 4,275,149 provides a review of some of these. The enzyme preferably catalyzes a chemical alteration of the chromogenic substrate that can be measured using various techniques. For example, the enzyme may catalyze a color change in a substrate, that can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase, beta-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

Examples of enzyme-substrate combinations include, for example:

(i) Horseradish peroxidase (HRP) with hydrogen peroxidase as a substrate, where the hydrogen peroxidase oxidizes a dye precursor (e.g. ABTS, orthophenylene diamine (OPD) or 3,3',5,5'-tetramethyl benzidine hydrochloride (TMB));

(ii) alkaline phosphatase (AP) with para-nitrophenyl phosphate as chromogenic substrate; and (iii) β-D-galactosidase (β-D-Gal) with a chromogenic substrate (e.g. p-nitrophenyl-β-D-galactosidase) or fluorogenic substrate 4-methylumbelliferyl-β-D-galactosidase.

According to a particular assay, the tracer is incubated with immobilized target in the presence of varying concentrations of unlabeled candidate compound. Increasing concentrations of successful candidate compound effectively compete with binding of the tracer to immobilized target. The concentration of unlabeled candidate compound at which 50% of the maximally-bound tracer is displaced is referred to as the "IC$_5$O" and reflects the IgG binding affinity of the candidate compound. Therefore a candidate compound with an IC$_{50}$ of 1 mM displays a substantially weaker interaction with the target than a candidate compound with an IC$_{50}$ of 104.

Accordingly, the disclosure provides albumin biding peptides "having the ability to compete" for target molecules such as human serum albumin binding in an in vitro assay as described. Preferably the albumin binding peptide has an IC$_{50}$ for the target such as human serum albumin of less than 1 µM. Preferred among these compound are compounds having an IC$_{50}$ of less than about 100 nM, and preferably less than about 10 nM or less than about 1 nM. In further preferred embodiments according to this aspect of the invention the compounds display an IC$_{50}$ for the target molecule such as or human serum albumin of less than about 100 pM and more preferably less than about 10 pM.

In some embodiments of the disclosure, exemplary albumin binding peptides include:

```
                                          (SEQ ID NO: 26)
D L C L R D W G C L W (SEQ ID NO: 27)
D I C L P R W G C L W (SEQ ID NO: 28)
M E D I C L P R W G C L W E D (SEQ ID NO: 29)
Q R L M E D I C L P R W G C L W E D D F (SEQ ID NO: 30)
Q G L I G D I C L P R W G C L W G D S V (SEQ ID NO: 31)
Q G L I G D I C L P R W G C L W G D S V K (SEQ ID NO: 32)
E D I C L P R W G C L W E D D (SEQ ID NO: 33)
R L M E D I C L P R W G C L W E D D (SEQ ID NO: 34)
M E D I C L P R W G C L W E DD (SEQ ID NO: 35)
M E D I C L P R W G C L W E D (SEQ ID NO: 36)
R L M E D I C L A R W G C L W E D D (SEQ ID NO: 37)
Q R L M E D I C L P R W G C L W E D D F
```

Examples of albumin binding peptides, methods of identifying them, and methods of making them are known in the art, see for example, US2004/0001827, incorporated herein by reference.

Cargo Molecules

In some embodiments, the cargo molecule of the albumin binding peptide conjugates of the disclosure is an immunomodulatory molecule. In some embodiments, an immunomodulatory molecule is an antigen, for example, a peptide antigen, protein antigen, polypeptide antigen. In some embodiments, an immunomodulatory molecule is a molecular adjuvant, for example, an immunostimulatory oligonucleotide. In some embodiments, the cargo can also be other oligonucleotides, peptides, Toll-like receptor agonists or other immunomodulatory compounds, immunostimulatory molecules, dyes, MRI contrast agents, fluorophores or small molecule drugs that require efficient trafficking to the lymph nodes.

In some embodiments, the cargo may be an adjuvant such as an immunostimulatory oligonucleotide, in some embodiments, the cargo molecule may be an antigen. An antigen may be a peptide, protein, polysaccharide, saccharide, lipid, nucleic acid, or combinations thereof. The antigen may be derived from a virus, bacterium, parasite, plant, protozoan, fungus, tissue or transformed cell such as a cancer or leukemic cell and can be a whole cell or immunogenic component thereof, e.g., cell wall components or molecular components thereof.

Suitable antigens are known in the art and are available from commercial government and scientific sources. In one embodiment, the antigens are cancer antigen peptides or molecular adjuvants. The antigens may be purified or partially purified peptides or polypeptides derived from tumors. In some embodiments, the antigens are recombinant peptide or polypeptides produced by expressing DNA encoding the peptide antigen or polypeptide antigen in a heterologous expression system. The antigens can be DNA encoding all or part of an antigenic protein, polypeptide or peptide. The DNA may be in the form of vector DNA such as plasmid DNA.

In certain embodiments, antigens are provided as single antigens or are provided in combination. In some embodiments, antigens are provided as complex mixtures of polypeptides, peptides or nucleic acids. Exemplary antigens are provided below.

a. Peptide Antigens

In certain embodiments, the albumin binding peptide (ABP) conjugates described herein may include an ABP operably coupled to a peptide antigen, antigenic protein, or antigenic polypeptide, such as a tumor-associated antigen or a fragment thereof.

In some embodiments, the peptide antigen can be 2-100 amino acids (aa), including for example, 5 amino acids, 10 amino acids, 15 amino acids, 20 amino acids, 25 amino acids, 30 amino acids, 35 amino acids, 40 amino acids, 45 amino acids, or 50 amino acids. In some embodiments, a peptide antigen can be greater than 50 amino acids. In some embodiments, the peptide antigen can be >100 amino acids.

In some embodiments, a protein/peptide antigen can be linear, branched or cyclic. The peptide antigen can include D amino acids, L amino acids, or a combination thereof. The peptide antigen, polypeptide antigen, or protein antigen can be conjugated to the ABP at the N-terminus or the C-terminus of the peptide antigen, polypeptide antigen, or protein antigen.

In some embodiments, the peptide antigen, protein antigen, or polypeptide antigen can be any peptide, protein, or polypeptide that can induce or increase the ability of the immune system to develop antibodies and T-cell responses to the peptide, protein, or polypeptide.

i. Cancer Antigens

In some embodiments, a peptide antigen may be generated from a cancer antigen. A cancer antigen is an antigen that is typically expressed preferentially by cancer cells (i.e., it is expressed at higher levels in cancer cells than on non-cancer cells) and in some instances it is expressed solely by cancer cells. The cancer antigen may be expressed within a cancer cell or on the surface of the cancer cell.

For example, the peptide antigen may be generated from any of the following cancer antigens: MART-1/Melan-A, gp100, adenosine deaminase-binding protein (ADAbp), FAP, cyclophilin b, colorectal associated antigen (CRC)-0017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain, and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A 10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-1, GAGE-2, GAGE-3, GAGE-4, GAGE-5, GAGE-6, GAGE-7, GAGE-8, GAGE-9, BAGE, RAGE, LAGE-1, NAG, GnT-V, MUM-1, CDK4, tyrosinase, p53, MUC family, HER2/neu, p21ras, RCAS1, a-fetoprotein, E-cadherin, a-catenin, β-catenin, γ-catenin, p120ctn, gp100Pmell 17, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, lmp-1, PI A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20, or c-erbB-2. Additional cancer antigens include the tumor antigens described herein.

In some embodiments, the peptide antigen is generated from a melanoma antigen. In some embodiments, the melanoma antigen is gp100. In some embodiments, the peptide antigen is an altered peptide ligand form of gp100 referred to as EGP. The amino acid sequence of EGP is (SEQ ID NO: 41)
AVGAL<u>EGPRNQDWL</u>GVPRQL, wherein the underlined portion has been shown to have high affinity for MHC over the native form.

In some embodiments, the albumin binding peptide conjugate stimulates an immune response against a specific target, such as a tumor-associated antigen.

In certain embodiments, a tumor-associated antigen is determined by sequencing a patient's tumor cells and identifying mutated proteins that are only found in the tumor. In some embodiments, a tumor-associated antigen is determined by analyzing a patient's tumor cells and identifying modified proteins (e.g., glycosylation, phosphorylation) that are only found in the tumor. These antigens are referred to as "neoantigens." Once a neoantigen has been identified, it can be used as the antigen for the albumin binding peptide conjugate or to derive a peptide antigen for an albumin binding peptide conjugate. In some embodiments, the ABP conjugates described herein include an ABP operably coupled with or without a linker domain to a neoantigen. In some embodiments, the ABP conjugates described herein include an ABP operably coupled with or without a linker domain to a peptide antigen derived from a neoantigen.

ii. Viral Antigens

In some embodiments, a peptide antigen may be generated from a viral antigen. A viral antigen can be isolated from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue D1NS3.

Viral antigens may be derived from a particular strain such as a papilloma virus, a herpes virus, e.g., herpes simplex 1 and 2; a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomeglavirus, Epstein-Barr, rotavirus, rhinovirus, adenovirus, coxsackieviruses, equine encephalitis, Japanese encephalitis, yellow fever, Rift Valley fever, and lymphocytic choriomeningitis.

iii. Bacterial Antigens

In some embodiments, a peptide antigen may be generated from a bacterial antigen. Bacterial antigens can originate from any bacteria including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus influenza* type B (HIB), *Hyphomicrobium, Legionella, Leptspirosis, Listeria*, Meningococcus A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus*, and *Treponema, Vibrio*, and *Yersinia*.

iv. Parasite Antigens

In other embodiments, a peptide antigen may be generated from a parasite antigen. Parasite antigens can be obtained from parasites such as, but not limited to, an antigen derived from *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni*. These include Sporozoan antigens, Plasmodian antigens, such as all or part of a Circumsporozoite protein, a Sporozoite surface protein, a liver stage antigen, an apical membrane associated protein, or a Merozoite surface protein.

v. Allergens and Environmental Antigens

In some embodiments, a peptide antigen can be generated from an allergen or environmental antigen. An allergen or environmental antigen, may be, for example, an antigen derived from naturally occurring allergens such as pollen allergens (tree-, herb, weed-, and grass pollen allergens), insect allergens (inhalant, saliva and venom allergens), animal hair and dandruff allergens, and food allergens. Important pollen allergens from trees, grasses and herbs originate from the taxonomic orders of Fagales, Oleales, Pinales and platanaceae including i.a. birch (*Betula\* alder (*Alnus*), hazel (*Corylus*), hornbeam (*Carpinus*) and olive (*Olea*), cedar {*Cryptomeria* and *Juniperus*), Plane tree (*Platanus*), the order of Poales including e.g., grasses of the genera *Lolium, Phleum, Poa, Cynodon, Dactylis, Holcus, Phalaris, Secale*, and *Sorghum*, the orders of Asterales and Urticales including i.a. herbs of the genera *Ambrosia, Artemisia*, and *Parietaria*. Other allergen antigens that may be used include allergens from house dust mites of the genus *Dermatophagoides* and *Euroglyphus*, storage mite e.g *Lepidoglyphys, Glycyphagus* and *Tyrophagus*, those from cockroaches, midges and fleas e.g. Blatella, *Periplaneta*, Chironomus and Ctenocepphalides, those from mammals such as cat, dog and horse, birds, venom allergens including such originating from stinging or biting insects such as those from the taxonomic order of Hymenoptera including bees (superfamily Apidae), wasps (superfamily Vespidea), and ants (superfamily Formicoidae). Still other allergen antigens that may be used include inhalation allergens from fungi such as from the genera *Alternaria* and *Cladosporium*.

b. Molecular Adjuvants

In certain embodiments, the albumin binding peptide (ABP) conjugates described herein may include an ABP operably coupled to a molecular adjuvant. In come embodiments, the molecular adjuvant is an immunostimulatory oligonucleotide, such as an oligonucleotide comprising CpG.

In some embodiments, the molecular adjuvant is an immunostimulatory oligonucleotides (e.g., an oligonucleotide comprising CpG) that can bind a pattern recognition receptor.

In some embodiments, the immunostimulatory oligonucleotide can serve as a ligand for pattern recognition receptors (PRRs). Examples of PRRs include the Toll-like family of signaling molecules that play a role in the initiation of innate immune responses and also influence the later and more antigen specific adaptive immune responses. Therefore, the oligonucleotide can serve as a ligand for a Toll-like family signaling molecule, such as Toll-Like Receptor 9 (TLR9).

For example, unmethylated CpG sites can be detected by TLR9 on plasmacytoid dendritic cells and B cells in humans (Zaida, et al., Infection and Immunity, 76(5):2123-2129, (2008)). Therefore, the sequence of oligonucleotide can include one or more unmethylated cytosine-guanine (CG or CpG, used interchangeably) dinucleotide motifs. The 'p' refers to the phosphodiester backbone of DNA, as discussed in more detail below, some oligonucleotides including CG can have a modified backbone, for example a phosphorothioate (PS) backbone.

In some embodiments, an immunostimulatory oligonucleotide can contain more than one CG dinucleotide, arranged either contiguously or separated by intervening nucleotides). The CpG motif(s) can be in the interior of the oligonucleotide sequence. Numerous nucleotide sequences stimulate TLR9 with variations in the number and location of CG dinucleotide(s), as well as the precise base sequences flanking the CG dimers.

Typically, CG ODNs are classified based on their sequence, secondary structures, and effect on human peripheral blood mononuclear cells (PBMCs). The five classes are Class A (Type D), Class B (Type K), Class C, Class P, and Class S (Vollmer, J & Krieg, A M, Advanced drug delivery reviews 61(3): 195-204 (2009), incorporated herein by reference). CG ODNs can stimulate the production of Type I interferons (e.g., IFNα) and induce the maturation of dendritic cells (DCs). Some classes of ODNs are also strong activators of natural killer (NK) cells through indirect cytokine signaling. Some classes are strong stimulators of human B cell and monocyte maturation (Weiner, G L, PNAS USA 94(20): 10833-7 (1997); Dalpke, A H, Immunology 106(1): 102-12 (2002); Hartmann, G, J of Immun. 164(3): 1617-2 (2000), each of which is incorporated herein by reference).

Other PRR Toll-like receptors include TLR3, and TLR7 which may recognize double-stranded RNA, single-stranded and short double-stranded RNAs, respectively, and retinoic acid-inducible gene I (RIG-I)-like receptors, namely RIG-I and melanoma differentiation-associated gene 5 (MDAS), which are best known as RNA-sensing receptors in the cytosol. Therefore, in some embodiments, the oligonucleotide contains a functional ligand for TLR3, TLR7, or RIG-I-like receptors, or combinations thereof.

Examples of immunostimulatory oligonucleotides, and methods of making them are known in the art, see for example, Bodera, P. Recent Pat Inflamm Allergy Drug Discov. 5(1):87-93 (2011), incorporated herein by reference.

In some embodiments, the oligonucleotide cargo includes two or more immunostimulatory sequences. The oligonucleotide can be between 2-100 nucleotide bases in length, including for example, 5 nucleotide bases in length, 10 nucleotide bases in length, 15 nucleotide bases in length, 20 nucleotide bases in length, 25 nucleotide bases in length, 30 nucleotide bases in length, 35 nucleotide bases in length, 40 nucleotide bases in length, 45 nucleotide bases in length, 50 nucleotide bases in length, 60 nucleotide bases in length, 70 nucleotide bases in length, 80 nucleotide bases in length, 90 nucleotide bases in length, 95 nucleotide bases in length, 98 nucleotide bases in length, 100 nucleotide bases in length or more.

The 3' end or the 5' end of the oligonucleotides can be conjugated to the albumin binding peptide (ABP). In a preferred embodiment the 5' end of the oligonucleotide is linked to the ABP.

The oligonucleotides can be DNA or RNA nucleotides which typically include a heterocyclic base (nucleic acid base), a sugar moiety attached to the heterocyclic base, and a phosphate moiety which esterifies a hydroxy 1 function of the sugar moiety. The principal naturally-occurring nucleotides comprise uracil, thymine, cytosine, adenine and guanine as the heterocyclic bases, and ribose or deoxyribose sugar linked by phosphodiester bonds.

In some embodiments, the oligonucleotides are composed of nucleotide analogs that have been chemically modified to improve stability, half-life, or specificity or affinity for a target receptor, relative to a DNA or RNA counterpart. The chemical modifications include chemical modification of nucleobases, sugar moieties, nucleotide linkages, or combinations thereof. As used herein 'modified nucleotide" or "chemically modified nucleotide" defines a nucleotide that has a chemical modification of one or more of the heterocyclic base, sugar moiety or phosphate moiety constituents. In some embodiments, the charge of the modified nucleotide is reduced compared to DNA or RNA oligonucleotides of the same nucleobase sequence. For example, the oligonucleotide can have low negative charge, no charge, or positive charge.

Typically, nucleoside analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). In some embodiments, the analogs have a substantially uncharged, phosphorus containing backbone.

i. Heterocyclic Bases

The principal naturally-occurring nucleotides include uracil, thymine, cytosine, adenine and guanine as the heterocyclic bases. The oligonucleotides can include chemical modifications to their nucleobase constituents. Chemical modifications of heterocyclic bases or heterocyclic base analogs may be effective to increase the binding affinity or stability in binding a target sequence. Chemically-modified heterocyclic bases include, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-ammo-5-(2'-deoxy-.beta.-D-ribofuranosyl)pyridine (2-aminopyridine), and various pyrrolo- and pyrazolopyrimidine derivatives. Cyclic dinucleotides known to trigger cytosolic danger sensors such as STING could be used.

ii. Sugar Modifications

Oligonucleotides can also contain nucleotides with modified sugar moieties or sugar moiety analogs. Sugar moiety modifications include, but are not limited to, 2'-O-aminoetoxy, 2'-O-amonioethyl (2'-OAE), 2'-O-methoxy, 2'-O-methyl, 2-guanidoethyl (2'-OGE), 2'-0,4'-C-methylene (LNA), 2'-O-(methoxyethyl) (2'-OME) and 2'-O-Wmethyl) acetamido) (2'-OMA). 2'-O-aminoethyl sugar moiety substitutions are especially preferred because they are protonated at neutral pH and thus suppress the charge repulsion between the TFO and the target duplex. This modification stabilizes the C3'-endo conformation of the ribose or dexyribose and also forms a bridge with the i-1 phosphate in the purine strand of the duplex.

In some embodiments, the oligonucleotide is a morpholino oligonucleotide. Morpholino oligonucleotides are typically composed of two more morpholino monomers containing purine or pyrimidine base-pairing moieties effective to bind, by base-specific hydrogen bonding, to a base in a polynucleotide, which are linked together by phosphorus-containing linkages, one to three atoms long, joining the morpholino nitrogen of one monomer to the 5' exocyclic carbon of an adjacent monomer. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337.

Important properties of the morpholino-based subunits typically include: the ability to be linked in a oligomeric form by stable, uncharged backbone linkages; the ability to support a nucleotide base (e.g. adenine, cytosine, guanine, thymidine, uracil or inosine) such that the polymer formed can hybridize with a complementary-base target nucleic acid, including target RNA, with high Tm, even with oligomers as short as 10-14 bases; the ability of the oligomer to be actively transported into mammalian cells; and the ability of an oligomer:RNA heteroduplex to resist RNAse degradation.

In some embodiments, oligonucleotides employ morpholino-based subunits bearing base-pairing moieties, joined by uncharged linkages, as described above.

iii. Internucleotide Linkages

Oligonucleotides connected by an internucleotide bond that refers to a chemical linkage between two nucleoside moieties. Modifications to the phosphate backbone of DNA or RNA oligonucleotides may increase the binding affinity or stability oligonucleotides, or reduce the suseptability of oligonucleotides nuclease digestion. Cationic modifications, including, but not limited to, diethyl-ethylenediamide (DEED) or dimethyl-aminopropylamine (DMAP) may be especially useful due to decrease electrostatic repulsion between the oligonucleotide and a target.

Modifications of the phosphate backbone may also include the substitution of a sulfur atom for one of the non-bridging oxygens in the phosphodiester linkage. This substitution creates a phosphorothioate internucleoside linkage in place of the phosphodiester linkage. Oligonucleotides containing phosphorothioate internucleoside linkages have been shown to be more stable in vivo.

Examples of modified nucleotides with reduced charge include modified internucleotide linkages such as phosphate analogs having achiral and uncharged intersubunit linkages (e.g., Sterchak, E. P. et al., Organic Chem., 52:4202, (1987)), and uncharged morpholino-based polymers having achiral intersubunit linkages (see, e.g., U.S. Pat. No. 5,034,506), as discussed above. Some internucleotide linkage analogs include morpholidate, acetal, and polyamide-linked heterocycles.

In another embodiment, the oligonucleotides are composed of locked nucleic acids. Locked nucleic acids (LNA) are modified RNA nucleotides (see, for example, Braasch, et al., Chem. Biol., 8(1): 1-7 (2001)). LNAs form hybrids with DNA which are more stable than DNA/DNA hybrids, a property similar to that of peptide nucleic acid (PNA)/DNA hybrids.

Therefore, LNA can be used just as PNA molecules would be. LNA binding efficiency can be increased in some embodiments by adding positive charges to it. Commercial nucleic acid synthesizers and standard phosphoramidite chemistry are used to make LNAs.

In some embodiments, the oligonucleotides are composed of peptide nucleic acids. Peptide nucleic acids (PNAs) are synthetic DNA mimics in which the phosphate backbone of the oligonucleotide is replaced in its entirety by repeating N-(2-aminoethyl)-glycine units and phosphodiester bonds are typically replaced by peptide bonds. The various heterocyclic bases are linked to the backbone by methylene carbonyl bonds. PNAs maintain spacing of heterocyclic bases that is similar to conventional DNA oligonucleotides, but are achiral and neutrally charged molecules. Peptide nucleic acids are comprised of peptide nucleic acid monomers.

Other backbone modifications include peptide and amino acid variations and modifications. Thus, the backbone constituents of oligonucleotides such as PNA may be peptide linkages, or alternatively, they may be non-peptide peptide linkages. Examples include acetyl caps, amino spacers such as 8-amino-3,6-dioxaoctanoic acid (referred to herein as O-linkers), amino acids such as lysine are particularly useful if positive charges are desired in the PNA, and the like. Methods for the chemical assembly of PNAs are well known. See, for example, U.S. Pat. Nos. 5,539,082, 5,527, 675, 5,623,049, 5,714,331, 5,736,336, 5,773,571 and 5,786, 571.

Oligonucleotides optionally include one or more terminal residues or modifications at either or both termini to increase stability, and/or affinity of the oligonucleotide for its target. Commonly used positively charged moieties include the amino acids lysine and arginine, although other positively charged moieties may also be useful. Oligonucleotides may further be modified to be end capped to prevent degradation using a propylamine group. Procedures for 3' or 5' capping oligonucleotides are well known in the art.

In some embodiments, the oligonucleotide is single-stranded DNA, single-stranded RNA, or double-stranded RNA.

c. Other Cargo

Generally, the cargo that can be conjugated to ABP can include immunomodulatory, therapeutic, prophylactic or diagnostic agents. For example, chemotherapy drugs are of interest for targeting tumors as albumin is known to accumulate in tumors by the EPR effect and also by fast metabolism in tumors.

In some embodiments, the ABP conjugates disclosed herein include a detection label, for example, a fluorophore such as fluorescein or rhodamine, Alexa Fluor dyes, DyLight Fluor dyes, Quasar and Cal Fluor dyes, cyanine dyes (Cy3, Cy5, Cy5.5, Cy7) or other fluorescent dyes. The label can be the cargo, or can be in addition to a cargo.

Linker Domains

In some embodiments, an albumin binding peptide conjugate includes a linker domain. In some embodiments, an albumin binding peptide conjugate includes a plurality of linker domains. In some embodiments, the linker domain is a polypeptide linker, an ethylene glycol linker, or an oligonucleotide linker. In certain aspects, it is desirable to employ a linker to fuse the albumin binding peptide, or a variant or fragment thereof, with one or more cargos, such as an immunomodulatory molecule (e.g., an antigen, a peptide antigen, or a molecular adjuvant) to form an albumin binding peptide conjugate.

The linkers of the invention may be employed, for instance, to ensure that an ABP is juxtaposed to ensure proper folding and formation of a functional immunomodulatory agent, or a variant or fragment thereof. Preferably, a linker compatible with the instant invention will be relatively non-immunogenic and not inhibit any non-covalent association among monomer subunits of a binding protein. Exemplary linker domains are disclosed in U.S. Pat. No. 6,660,843, which is incorporated by reference herein.

In some embodiments, the linker may be a non-cleavable linker or a cleavable linker. A non-cleavable linker may include an amide bond or phosphate bond, and the cleavable linker may include a disulfide bond, acid-cleavable linkage, ester bond, anhydride bond, biodegradable bond, or enzyme-cleavable linkage.

a. Polypeptide Linkers

In certain embodiments, the albumin binding peptide conjugates of the invention employ a polypeptide linker to join any two or more domains in frame in a single polypeptide chain. In one embodiment, the two or more domains may be independently selected from any of the albumin binding peptides, or variants or fragments thereof, or cargo molecules discussed herein. For example, in certain embodiments, a polypeptide linker can be used to fuse an albumin binding peptide to an immunomodulatory molecule (e.g., a peptide antigen or a molecular adjuvant).

In some embodiments, the polypeptide linker is synthetic. As used herein, the term "synthetic" with respect to a polypeptide linker includes peptides (or polypeptides) which comprise an amino acid sequence (which may or may not be naturally occurring) that is linked in a linear sequence of amino acids to a sequence (which may or may not be naturally occurring) (e.g., an ABP sequence) to which it is not naturally linked in nature. For example, the polypeptide linker may comprise non-naturally occurring polypeptides which are modified forms of naturally occurring polypeptides (e.g., comprising a mutation such as an addition, substitution or deletion) or which comprise a first amino acid sequence (which may or may not be naturally occurring).

In some embodiments, a polypeptide linker comprises or consists of a gly-ser linker. As used herein, the term "gly-ser linker" refers to a peptide that consists of glycine and serine residues. An exemplary gly/ser linker comprises an amino acid sequence of the formula $(Gly_4Ser)_n$ (SEQ ID NO: 44), wherein n is a positive integer (e.g., 1, 2, 3, 4, or 5). In certain embodiments the gly/ser linker is $(Gly_4Ser)_1$ (SEQ ID NO: 42). In certain embodiments the gly/ser linker is $(Gly_4Ser)_2$. In certain embodiments the gly/ser linker is $(Gly_4Ser)_3$ (SEQ ID NO: 44). In certain embodiments the gly/ser linker is (Gly$_4$Ser)$_4$ (SEQ ID NO: 44). In certain embodiments the gly/ser linker is (Gly$_4$Ser)$_5$ (SEQ ID NO: 44). In certain embodiments, the gly-ser linker may be inserted between two other sequences of the polypeptide linker (e.g., any of the polypeptide linker sequences described herein). In other embodiments, a gly-ser linker is attached at one or both ends of another sequence of the polypeptide linker (e.g., any of the polypeptide linker sequences described herein). In yet other embodiments, two or more gly-ser linker are incorporated in series in a polypeptide linker.

Other linkers that are suitable for use in the albumin binding peptide conjugates are known in the art, for example, the serine-rich linkers disclosed in U.S. Pat. No. 5,525,491, the helix forming peptide linkers (e.g., A(EAAAK)nA (n=2-5)) (SEQ ID NO: 45) disclosed in Arai et al., Protein Eng 2001; 14:529-32, and the stable linkers disclosed in Chen et al., Mol Pharm 2011; 8:457-65, i.e., the dipeptide linker LE, a thrombin-sensitive disulfide cyclopeptide linker, and the alpha-helix forming linker LEA (EAAAK)$_4$ALEA(EAAAK)$_4$ALE (SEQ ID NO: 38).

Other exemplary linkers include GS linkers (i.e., (GS)n), GGSG (SEQ ID NO: 39) linkers (i.e., (GGSG)n (SEQ ID NO: 46)), GSAT (SEQ ID NO: 40) linkers, SEG linkers, and GGS linkers (i.e., (GGSGGS)n (SEQ ID NO: 47)), wherein n is a positive integer (e.g., 1, 2, 3, 4, or 5). Other suitable linkers for use in the albumin binding peptide conjugates can be found using publicly available databases, such as the Linker Database (ibi.vu.nl/programs/linkerdbwww). The Linker Database is a database of inter-domain linkers in multi-functional enzymes which serve as potential linkers in novel fusion proteins (see, e.g., George et al., *Protein Engineering* 2002; 15:871-9).

It will be understood that variant forms of these exemplary polypeptide linkers can be created by introducing one or more nucleotide substitutions, additions or deletions into the nucleotide sequence encoding a polypeptide linker such that one or more amino acid substitutions, additions or deletions are introduced into the polypeptide linker. Mutations may be introduced by standard techniques, such as site-directed mutagenesis and PCR-mediated mutagenesis.

Polypeptide linkers of the invention are at least one amino acid in length and can be of varying lengths. In one embodiment, a polypeptide linker of the invention is from about 1 to about 50 amino acids in length. As used in this context, the term "about" indicates +/–two amino acid residues. Since linker length must be a positive integer, the length of from about 1 to about 50 amino acids in length, means a length of from 1 to 48-52 amino acids in length. In another embodiment, a polypeptide linker of the invention is from about 1-5 amino acids in length. In another embodiment, a polypeptide linker of the invention is from about 5-10 amino acids in length. In another embodiment, a polypeptide linker of the invention is from about 10-20 amino acids in length. In another embodiment, a polypeptide linker of the invention is from about 15 to about 50 amino acids in length.

In another embodiment, a polypeptide linker of the invention is from about 20 to about 45 amino acids in length. In another embodiment, a polypeptide linker of the invention is from about 15 to about 25 amino acids in length. In another embodiment, a polypeptide linker of the invention is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or 61 or more amino acids in length.

Polypeptide linkers can be introduced into polypeptide sequences using techniques known in the art. Modifications can be confirmed by DNA sequence analysis. Plasmid DNA can be used to transform host cells for stable production of the polypeptides produced.

b. Ethylene Glycol Linkers

In some embodiments, the linker domain is one or more ethylene glycol (EG) units, more preferably 2 or more EG units (i.e., polyethylene glycol (PEG)). In some embodiments, a linker domain comprises or consists of a polyethylene glycol (PEG) linker. Polyethylene glycol or PEG refers to a chemical compound composed of repeating ethylene glycol units. An exemplary "PEG linker" comprises a compound of the formula: H—(O—CH2-CH2)n-OH, wherein n is a positive integer (e.g., 1, 10, 20, 50, 100, 200, 300, 400, 500, 600). In some embodiments, the PEG linker is PEG1000. In some embodiments, the PEG linker is PEG2000. In some embodiments, the PEG linker is PEG3000.

In some embodiments, an albumin binding peptide conjugate includes an immunomodulatory molecular (e.g., a peptide antigen) linked to a polyethylene glycol (PEG) molecule which is in turn linked to an albumin binding peptide.

The precise number of ethylene glycol (EG) units depends on the albumin binding peptide and the cargo, however, typically, an ethylene glycol linker can have between about 1 and about 100, between about 20 and about 80, between about 30 and about 70, or between about 40 and about 60 EG units. In some embodiments, the ethylene glycol linker has between about 45 and 55 EG, units. For example, in one embodiment, the ethylene glycol linker has 45 EG units. For example, in one embodiment, the ethylene glycol linker has 48 EG units.

c. Oligonucleotide Linkers

In some embodiments, the linker is an oligonucleotide. The linker can be have any sequence, for example, the sequence of the oligonucleotide can be a random sequence, or a sequence specifically chosen for its molecular or biochemical properties. In some embodiments, the linker includes one or more series of consecutive adenine (A), cytosine (C), guanine (G), thymine (T), uracil (U), or analog thereof. In some embodiments, the linker consists of a series of consecutive adenine (A), cytosine (C), guanine (G), thymine (T), uracil (U), or analog thereof.

In one embodiment, the linker is one or more guanines, for example between 1-10 guanines. In some embodiments, the linker in an ABP conjugate can include 0, 1, or 2 guanines.

Immunogenic Compositions

In some embodiments, the albumin binding peptide conjugates of the present disclosure may be used in immunogenic compositions or as components in vaccines. In some embodiments, the immunogenic compositions disclosed herein include an albumin binding peptide conjugate. In some embodiments, the immunogenic compositions disclosed herein include a combination of an albumin binding peptide conjugate and an adjuvant. The combination of an adjuvant and an albumin binding peptide conjugate can be referred to as a vaccine. When administered to a subject in combination, the adjuvant and albumin binding peptide conjugate can be administered in separate pharmaceutical compositions, or they can be administered together in the same pharmaceutical composition.

An immunogenic composition can include an albumin binding peptide conjugate, such as an albumin binding peptide that is an linked to an immunomodulatory molecule (e.g., a peptide antigen or molecular adjuvant) administered alone, or in combination with an adjuvant.

The adjuvant may be without limitation alum (e.g., aluminum hydroxide, aluminum phosphate); saponins purified from the bark of the *Q. saponaria* tree such as QS21 (a glycolipid that elutes in the 21st peak with HPLC fractionation; Antigenics, Inc., Worcester, Mass.); poly[di(carboxylatophenoxy)phosphazene (PCPP polymer; Virus Research Institute, USA), Flt3 ligand, *Leishmania* elongation factor (a purified *Leishmania* protein; Corixa Corporation, Seattle, Wash.), ISCOMS (immunostimulating complexes which contain mixed saponins, lipids and form virus-sized particles with pores that can hold antigen; CSL, Melbourne, Australia), Pam3Cys, SB-AS4 (SmithKline Beecham adjuvant system #4 which contains alum and MPL; SBB, Belgium), non-ionic block copolymers that form micelles such as CRL 1005 (these contain a linear chain of hydrophobic polyoxypropylene flanked by chains of polyoxyethylene, Vaxcel, Inc., Norcross, Ga.), and Montanide IMS (e.g., IMS 1312, water-based nanoparticles combined with a soluble immunostimulant, Seppic).

Adjuvants may be TLR ligands, such as those discussed herein. Adjuvants that act through TLR3 include without limitation double-stranded RNA. Adjuvants that act through TLR4 include without limitation derivatives of lipopoly saccharides such as monophosphoryl lipid A (MPL A; Ribi ImmunoChem Research, Inc., Hamilton, Mont.) and muramyl dipeptide (MDP; Ribi) andthreonyl-muramyl dipeptide (t-MDP; Ribi); OM-174 (a glucosamine disaccharide related to lipid A; OM Pharma S A, Meyrin, Switzerland). Adjuvants that act through TLR5 include without limitation flagellin. Adjuvants that act through TLR7 and/or TLR8 include single-stranded RNA, oligoribonucleotides (ORN), synthetic low molecular weight compounds such as imidazoquinolinamines (e.g., imiquimod (R-837), resiquimod (R-848)). Adjuvants acting through TLR9 include DNA of viral or bacterial origin, or synthetic oligodeoxynucleotides (ODN), such as CpG ODN. Another adjuvant class is phosphorothioate containing molecules such as phosphorothioate nucleotide analogs and nucleic acids containing phosphorothioate backbone linkages.

The adjuvant can also be oil emulsions (e.g., Freund's adjuvant); saponin formulations; virosomes and viral-like particles; bacterial and microbial derivatives; immunostimulatory oligonucleotides; ADP-ribosylating toxins and detoxified derivatives; alum; BCG; mineral-containing compositions (e.g., mineral salts, such as aluminium salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

Adjuvants may also include immunomodulators such as cytokines, interleukins (e.g., IL-1, IL-2, IL-4, IL-5, IL-6, IL-7, IL-12, etc.), interferons (e.g., interferon-.gamma.), macrophage colony stimulating factor, and tumor necrosis factor.

Pharmaceutical Compositions and Modes of Administration

In certain embodiments, an albumin binding peptide conjugate is administered to a subject in need thereof.

In some embodiments, the disclosure provides pharmaceutical compositions comprising albumin binding peptide conjugates. In certain embodiments, the disclosure provides for a pharmaceutical composition comprising an albumin binding peptide conjugate and a pharmaceutically acceptable diluent, carrier, solubilizer, emulsifier, preservative and/or adjuvant.

Pharmaceutical compositions can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some embodiments, the compositions are administered systemically, for example, by intravenous or intraperitoneal administration, in an amount effective for delivery of the compositions to targeted cells. Other possible routes include trans-dermal or oral.

In certain embodiments, the compositions are administered locally, for example by injection directly into a site to be treated. In some embodiments, the compositions are injected or otherwise administered directly to one or more tumors. Typically, local injection causes an increased localized concentration of the compositions which is greater than that which can be achieved by systemic administration. In some embodiments, the compositions are delivered locally to the appropriate cells by using a catheter or syringe. Other means of delivering such compositions locally to cells include using infusion pumps (for example, from Alza Corporation, Palo Alto, Calif.) or incorporating the compositions into polymeric implants (see, for example, P. Johnson and J. G. Lloyd-Jones, eds., Drug Delivery Systems (Chichester, England: Ellis Horwood Ltd., 1987), which can effect a sustained release of the nanolipogels to the immediate area of the implant.

In certain embodiments, acceptable formulation materials preferably are nontoxic to recipients at the dosages and concentrations employed. In certain embodiments, the formulation material(s) are for s.c. and/or I.V. administration. In certain embodiments, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In certain embodiments, the formulation comprises PBS; 20 mM NaOAC, pH 5.2, 50 mM NaCl; and/or 10 mM NAOAC, pH 5.2, 9% Sucrose. In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and rate of in vivo clearance of the albumin binding peptide conjugate.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In certain embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising an albumin binding peptide conjugate, can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising an albumin binding peptide conjugate, can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In some embodiments, the albumin binding peptide conjugates of the disclosure are administered in an aqueous solution, by parenteral injection. In some embodiments, the composition includes albumin, or other serum proteins.

In some embodiments, the formulation can be in the form of a suspension or emulsion. In general, pharmaceutical compositions are provided including an effective amount of the albumin biding peptide conjugate and optionally include pharmaceutically acceptable diluents, preservatives, solubilizers, emulsifiers, adjuvants and/or carriers. Such compositions can include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

In certain embodiments, when parenteral administration is contemplated, a therapeutic composition can be in the form of a pyrogen-free, parenterally acceptable aqueous solution comprising an albumin binding peptide conjugate, in a pharmaceutically acceptable vehicle. In certain embodiments, a vehicle for parenteral injection is sterile distilled water in which an albumin binding peptide conjugate is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In some embodiments, the albumin binding peptide conjugates of the disclosure can be applied topically. Topical administration can include application to the lungs (pulmonary), nasal, oral (sublingual, buccal), vaginal, or rectal mucosa. In some cases, the conjugates may be transcytosed on albumin across mucosal barriers.

In certain embodiments, a pharmaceutical composition can be formulated for inhalation. In certain embodiments, an albumin binding peptide conjugate can be formulated as a dry powder for inhalation. In certain embodiments, an inhalation solution comprising an albumin binding peptide conjugate can be formulated with a propellant for aerosol delivery. In certain embodiments, solutions can be nebulized. Pulmonary administration is further described in PCT application No. PCT/US94/001875, which describes pulmonary delivery of chemically modified proteins.

In certain embodiments, compositions can be delivered to the lungs while inhaling and traverse across the lung epithelial lining to the blood stream when delivered either as an aerosol or spray dried particles having an aerodynamic diameter of less than about 5 microns. A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent® nebulizer (Mallinckrodt Inc., St. Louis, Mo.); the Acorn® II nebulizer (Marquest Medical Products, Englewood, Colo.); the Ventolin® metered dose inhaler (Glaxo Inc., Research Triangle Park, N.C.); and the Spinhaler® powder inhaler (Fisons Corp., Bedford, Mass.). Nektar, Alkermes and Mannkind all have inhalable insulin powder preparations approved or in clinical trials where the technology could be applied to the formulations described herein.

In certain embodiments, it is contemplated that formulations can be administered orally. In certain embodiments, an albumin binding peptide conjugate that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of an albumin binding peptide conjugate. In certain embodiments, diluents, flavorings, low melting point waxes, vegetable oils, lubricants, suspending agents, tablet disintegrating agents, and binders can also be employed.

In some embodiments, formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets, capsules, or lozenges. In some embodiments, transdermal formulations may also be prepared. These will typically be ointments, lotions, sprays, or patches, all of which can be prepared using standard technology. Transdermal formulations can include penetration enhancers.

In certain embodiments, a pharmaceutical composition can involve an effective quantity of an albumin binding peptide conjugate in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving an albumin binding peptide conjugate in sustained- or controlled-delivery formulations. In certain embodiments, techniques for formulating a variety of other sustained- or controlled-delivery means, such as liposome carriers, bioerodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15: 167-277 (1981) and Langer, Chem. Tech., 12:98-105 (1982)), ethylene vinyl acetate (Langer et al., supra) or poly-D(−)-3-hydroxybutyric acid (EP 133,988). In certain embodiments, sustained release compositions can also include liposomes, which can be prepared by any of several methods known in the art. See, e.g., Eppstein et al, Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried compound and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising an albumin binding peptide conjugate to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which an albumin binding peptide conjugate is being used, the route of administration, and the size (body weight, body surface or organ size) and/or condition (the age and general health) of the patient. In certain embodiments, the clinician can titer the dosage and modify the route of administration to obtain the optimal therapeutic effect. In certain embodiments, a typical dosage for an albumin binding peptide conjugate can range from about 0.1 µg/kg to up to about 10 mg/kg or more, depending on the factors mentioned above. In certain embodiments, the dosage can range from 0.1 µg/kg up to about 10 mg/kg; or 0.1 µg/kg up to about 1 mg/kg; or 0.1 µg/kg up to about 0.1 mg/kg; or 0.1 µg/kg up to about 0.05 mg/kg; or 0.1 µg/kg up to about 0.01 mg/kg.

In certain embodiments, the frequency of dosing will take into account the pharmacokinetic parameters of the albumin binding peptide conjugate in the formulation used. In certain embodiments, a clinician will administer the composition until a dosage is reached that achieves the desired effect. In certain embodiments, the composition can therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device. In certain embodiments, individual elements of the combination therapy may be administered by different routes.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration. In certain embodiments, it can be desirable to use a pharmaceutical composition comprising an albumin binding peptide conjugate in an ex vivo manner. In such instances, cells, tissues and/or organs that have been removed from the patient are exposed to a pharmaceutical composition comprising an albumin binding peptide conjugate after which the cells, tissues and/or organs are subsequently implanted back into the patient.

In certain embodiments, an albumin binding peptide conjugate can be delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the albumin binding peptide conjugate(s) but prevent the destruction of the cells by the patient's immune system or by other detrimental factors from the surrounding tissues.

Methods of Making Albumin Binding Peptide Conjugates

In some aspects, the albumin binding peptide conjugates described herein may be made in transformed host cells using recombinant DNA techniques. To do so, a recombinant DNA molecule coding for the albumin binding peptide conjugate is prepared. Methods of preparing such DNA molecules are well known in the art. For instance, sequences coding for the albumin binding peptide conjugate could be excised from DNA using suitable restriction enzymes. Alternatively, the DNA molecule could be synthesized using chemical synthesis techniques, such as the phosphoramidate method. Also, a combination of these techniques could be used.

The methods of making albumin binding peptide conjugates also include a vector capable of expressing the albumin binding peptide conjugates in an appropriate host. The vector comprises the DNA molecule that codes for the albumin binding peptide conjugate operatively linked to appropriate expression control sequences. Methods of affecting this operative linking, either before or after the DNA molecule is inserted into the vector, are well known. Expression control sequences include promoters, activators, enhancers, operators, ribosomal nuclease domains, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be suitable for use in the methods disclosed herein. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial hosts include bacteria (such as *E. coli* sp.), yeast (such as *Saccharomyces* sp.) and other fungi, insects, plants, mammalian (including human) cells in culture, or other hosts known in the art.

Next, the transformed host is cultured and purified. Host cells may be cultured under conventional fermentation conditions so that the desired compounds are expressed. Such fermentation conditions are well known in the art. Finally, the peptides are purified from culture by methods well known in the art.

The compounds may also be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. In some embodiments, solid phase synthesis is a technique for making albumin binding peptide conjugates. Compounds that contain derivatized peptides or which contain non-peptide groups may be synthesized by well-known organic chemistry techniques.

In some embodiments, the albumin binding peptide conjugates may be generated via solid-phase peptide synthesis. In some embodiments, an automated synthesizer or manual solid-phase peptide synthesis techniques are used to synthesize the ABP conjugates. In certain embodiments, solution peptide synthesis may be used to synthesize the ABP conjugates.

In some embodiments, the domains of the albumin binding peptide conjugate are synthesized as separate units or domains. In some embodiments, the domains of the albumin binding peptide conjugates are synthesized as a single unit.

For example, in some embodiments, an albumin binding peptide conjugate comprising an albumin binding peptide linked with or without a linker domain to a molecular adjuvant may be synthesized in two separate units, using automated solid-phase peptide synthesis for the ABP and DNA synthesis for the molecular adjuvant (e.g., CpG antigen). The two components may then be coupled in solution via Cu(I)-catalyzed click chemistry. Other methods generally known in the art for solid phase peptide synthesis techniques could be employed to synthesize the ABP component. Other synthetic techniques generally known in the art could be used to synthesize the adjuvant molecule (For example, DNA synthesis variations generally known in the art for the CpG domain and other DNA adjuvants, otherwise varying with the nature of the molecular antigen). Bioconjugation strategies generally known in the art (for example, (amide/NHS ester, sulfhydryl/maleimide, azide/DBCO, and others) could be employed to link the two components of the ABP conjugate.

In some embodiments, an albumin binding peptide conjugate comprising an albumin binding peptide linked with or without a linker domain to an antigen (e.g., a peptide antigen) may be synthesized as a single unit.

Other methods of molecule expression/synthesis are generally known in the art to one of ordinary skill.

Expression of Polypeptides

The nucleic acid molecules described above can be contained within a vector that is capable of directing their expression in, for example, a cell that has been transduced with the vector. Accordingly, expression vectors containing a nucleic acid molecule encoding a albumin binding peptide conjugate and cells transfected with these vectors are among the certain embodiments.

Vectors suitable for use include T7-based vectors for use in bacteria (see, for example, Rosenberg et al., Gene 56: 125, 1987), the pMSXND expression vector for use in mammalian cells (Lee and Nathans, J. Biol. Chem. 263:3521, 1988), and baculovirus-derived vectors (for example the expression vector pBacPAKS from Clontech, Palo Alto, Calif.) for use in insect cells. The nucleic acid inserts, which encode the polypeptide of interest in such vectors, can be operably linked to a promoter, which is selected based on, for example, the cell type in which expression is sought. For example, a T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance (neo$^r$) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that are suitable for use include, for example, retroviral, adenoviral, and adeno-associated vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.).

Prokaryotic or eukaryotic cells that contain and express a nucleic acid molecule that encode an albumin binding peptide conjugate are also suitable for use. A cell is a transfected cell, i.e., a cell into which a nucleic acid molecule, for example a nucleic acid molecule encoding a an albumin binding peptide conjugate, has been introduced by means of recombinant DNA techniques. The progeny of such a cell are also considered suitable for use in the methods disclosed herein.

The precise components of the expression system are not critical. For example, an albumin binding peptide conjugate can be produced in a prokaryotic host, such as the bacterium E. coli, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

The expressed an albumin binding peptide conjugates can be purified from the expression system using routine biochemical procedures, and can be used, e.g., as therapeutic agents, as described herein.

Methods of Use a. Methods of Delivering Albumin Binding Peptide Conjugates i. Lymph Node Targeting In some embodiments, the disclosure provides that conjugating a cargo such as an immunomodulatory molecule (e.g., an antigenic peptide), to an albumin binding peptide (ABP) may increase delivery and accumulation of the cargo to the lymph nodes. The lymph nodes are oval-shaped organs of the immune system, distributed widely throughout the body including the armpit and stomach and linked by lymphatic vessels. Lymph nodes are bastions of B, T, and other immune cells. Lymph nodes act as filters or traps for foreign particles and are important in the proper functioning of the immune system. They are packed tightly with the white blood cells called lymphocytes and macrophages.

Lymph node targeting conjugates may be transported from the injection site to secondary organs of the lymphatic system (e.g., lymph nodes), where interact with immune cells. It is believed that albumin-binding of the ABP-conjugates prevents the ABP-conjugates from rapidly flushing into the bloodstream and re-targets them to lymphatics and draining lymph nodes, where they are filtered, accumulate, and present their cargo (e.g., an immunomodulatory molecule, such as a peptide antigen or molecular adjuvant) to immune cells.

As discussed above, albumin binding peptides may be conjugated to, for example, an immunomodulatory molecule (e.g., a peptide antigen or a molecular adjuvant) which increases the immunostimulatory effect of the immunomodulatory molecule (e.g., a peptide antigen or a molecular adjuvant) compared to administering non-conjugated immunomodulatory molecule (e.g., a peptide antigen or a molecular adjuvant). In some embodiments, conjugation of the cargo (e.g., immunomodulatory molecule) to the albumin binding peptide increases accumulation of the cargo 2, 3, 4, 5, 6, 7, 8, 9, 10, or more fold compare to unconjugated cargo.

ii. Tissue Specific Targeting

Albumin binding peptide conjugates can be used to increase delivery and accumulation of the cargo (e.g., antigenic peptides, molecular adjuvants) to the tissue at or near a site of administration. In some embodiments, the albumin binding peptide conjugates can accumulate at the site of injection. In some embodiments, the albumin binding peptide conjugates may be targeted to, for example, mucosal tissues.

b. Methods of Increasing an Immune Response

Albumin binding peptide conjugates including an immunomodulatory molecule (e.g., a peptide antigen or a molecular adjuvant) may be administered in an effective amount to induce, increase or enhance an immune response. The "immune response" refers to responses that induce, increase, induce, or perpetuate the activation or efficiency of innate or adaptive immunity. Further, albumin binding peptide conjugates administered in the absence of other adjuvants may be used to promote tolerance rather than immunity, e.g., to an allergen or autoimmune antigen.

The ABP-conjugates can be delivered parenterally (by subcutaneous, intradermal, or intramuscular injection) through the lymphatics, or by systemic administration through the circulatory system. The lymph nodes may filter albumin-bound conjugates. Therefore, in some embodiments parenteral administration does not result in systemic distribution as the ABP-conjugates may be preferentially filtered by the closest lymph node(s). This tendency also reduces systemic toxicity such as swelling of the spleen.

Accordingly, in some embodiments, the ABP-conjugates are administered at a site adjacent to or leading to one or more lymph nodes which are close to the site in need of an immune response (i.e., close to a tumor or site of infection). In some embodiments, the ABP-conjugates are administered in multiple doses at various locations throughout the body. In some embodiments, the ABP-conjugates can also be administered directly to a site in need of an immune response (e.g., a tumor or site of infection).

The immune response may be induced, increased, or enhanced by the ABP-conjugate compared to a control, for example an immune response in a subject induced, increased, or enhanced by the cargo alone, or the cargo delivered using an alternative delivery strategy such as liposomes. In some embodiments, ABP-conjugates reduce inactivation and/or prolong activation of T cells (i.e., increase antigen-specific proliferation of T cells, enhance cytokine production by T cells, stimulate differentiation ad effector functions of T cells and/or promote T cell survival) or overcome T cell exhaustion and/or anergy.

The ABP-conjugates may be used, for example, to induce an immune response, when administering the cargo alone, or the cargo in combination with an alternative delivery system, is ineffectual. The ABP-conjugates may also be used to enhance or improve the immune response compared to administering cargo alone. In some embodiments, the ABP-conjugates may reduce the dosage required to induce, increase, or enhance an immune response; or reduce the time needed for the immune system to respond following administration.

ABP-conjugates may be administered as part of prophylactic vaccines or immunogenic compositions which confer resistance in a subject to subsequent exposure to infectious agents, or as part of therapeutic vaccines, which can be used to initiate or enhance a subject's immune response to a pre-existing antigen, such as a viral antigen in a subject infected with a virus or with cancer.

The desired outcome of a prophylactic or therapeutic immune response may vary according to the disease or condition to be treated, or according to principles well known in the art. For example, an immune response against an infectious agent may completely prevent colonization and replication of an infectious agent, affecting "sterile immunity" and the absence of any disease symptoms. However, a vaccine against infectious agents may be considered effective if it reduces the number, severity or duration of symptoms; if it reduces the number of individuals in a population with symptoms; or reduces the transmission of an infectious agent.

Similarly, immune responses against cancer, allergens or infectious agents may completely treat a disease, may alleviate symptoms, or may be one facet in an overall therapeutic intervention against a disease.

The ABP-conjugates may induce an improved effector cell response such as a CD4 T-cell immune response, against at least one of the component antigen(s) or antigenic compositions compared to the effector cell response obtained with the corresponding composition without the ABP-conjugate. The term "improved effector cell response" refers to a higher effector cell response such as a CD8 or CD4 response obtained in a human patient after administration of the ABP-conjugate than that obtained after administration of the same cargo without a ABP-conjugate.

The improved effector cell response can be obtained in an immunologically unprimed patient, i.e. a patient who is seronegative to the antigen. This seronegativity may be the result of the patient having never faced the antigen (so-called "naive" patient) or, alternatively, having failed to respond to the antigen once encountered. In some embodiments, the improved effector cell response is obtained in an immunocompromised subject.

The improved effector cell response can be assessed by measuring the number of cells producing any of the following cytokines: (1) cells producing at least two different cytokines (CD40L, IL-2, IFN-gamma, TNF-alpha); (2) cells producing at least CD40L and another cytokine (IL-2, TNF-alpha, IFN-gamma); (3) cells producing at least IL-2 and another cytokine (CD40L, TNF-alpha, IFN-gamma); (4) cells producing at least IFN-gamma and another cytokine (IL-2, TNF-alpha, CD40L); (5) and cells producing at least TNF-alpha and another cytokine (IL-2, CD40L, IFN-gamma). An improved effector cell response is present when cells producing any of the above cytokines will be in a higher amount following administration of the ABP-conjugate composition compared to control as discussed above.

In some embodiments, the ABP-conjugate increases the number of T cells producing IFN-gamma, TNF-alpha, or a combination thereof, or increases the production of IFN-gamma, TNF-alpha, or a combination thereof in the existing T cells.

In some embodiments, the administration of the immunogenic composition alternatively or additionally induces an improved B-memory cell response in patients administered ABP-conjugates compared to a control. An improved B-memory cell response is intended to mean an increased frequency of peripheral blood B lymphocytes capable of differentiation into antibody-secreting plasma cells upon antigen encounter as measured by stimulation of in vitro differentiation.

In other embodiments, the immunogenic composition increases the primary immune response as well as the CD8 response. The administration of the ABP-conjugate induces an improved CD4 T-cell, or CD8 T-cell immune response against a specific antigen compared to a control. This method may allow for inducing a CD4 T cell response which is more persistent in time.

In some embodiments, the CD4 T-cell immune response, such as the improved CD4 T-cell immune response obtained in an unprimed subject, involves the induction of a cross-reactive CD4 T helper response. In particular, the amount of cross-reactive CD4 T cells is increased. The term "cross-reactive" CD4 response refers to CD4 T-cell targeting shared epitopes for example between influenza strains.

It will be appreciated by those skilled in the art that amount of the albumin binding peptide conjugate that is sufficient to stimulate or enhance an immune response, or a therapeutically effective amount, will vary not only on the particular compounds or compositions selected, but also with the route of administration, the nature of the condition being treated, and the age and condition of the patient, and will ultimately be at the discretion of the patient's physician or pharmacist. The length of time during which the compounds used in the instant method will be given varies on an individual basis.

c. Diseases to Be Treated i. Cancer

The albumin binding peptide (ABP) conjugates of the disclosure are useful for stimulating or enhancing an immune response in for treating cancer. In some embodiments, the albumin binding peptide conjugate may be used as an anti-cancer vaccine. Accordingly, the compositions used herein, comprising, e.g., an albumin binding peptide conjugate, can be administered to a patient who has cancer.

The types of cancer that may be treated with the provided compositions and methods include, but are not limited to, the following: bladder, brain, breast, cervical, colo-rectal, esophageal, kidney, liver, lung, nasopharangeal, pancreatic, prostate, skin (e.g., melanoma), stomach, uterine, ovarian, testicular and hematologic. Other non-limiting examples of cancers that are amenable to treatment with the compositions and methods of the present disclosure are described herein.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The ABP-conjugates can be administered in as an immunogenic composition or as part of vaccine, such as prophylactic vaccines, or therapeutic vaccines, which can be used to initiate or enhance a subject's immune response to a pre-existing antigen, such as a tumor antigen in a subject with cancer.

The desired outcome of a prophylactic or therapeutic immune response may vary according to the disease, according to principles well known in the art. Similarly, immune responses against cancer, may alleviate symptoms, or may be one facet in an overall therapeutic intervention against a disease. For example, administration of the ABP-conjugates may reduce tumor size, or slow tumor growth compared to a control. The stimulation of an immune response against a cancer may be coupled with surgical, chemotherapeutic, radiologic, hormonal and other immunologic approaches in order to affect treatment.

ii. Infectious Diseases

In some embodiments, the ABP-conjugates of the disclosure are useful for treating acute or chronic infectious diseases. Because viral infections are cleared primarily by T-cells, an increase in T-cell activity is therapeutically useful in situations where more rapid or thorough clearance of an infective viral agent would be beneficial to an animal or human subject. Thus, the ABP-conjugates antagonists can be administered for the treatment of local or systemic viral infections, including, but not limited to, immunodeficiency (e.g., HIV), papilloma (e.g., HPV), herpes (e.g., HSV), encephalitis, influenza (e.g., human influenza virus A), and common cold (e.g., human rhinovirus) viral infections. For example, pharmaceutical formulations including the ABP-conjugates can be administered topically to treat viral skin diseases such as herpes lesions or shingles, or genital warts. The ABP-conjugates can also be administered to treat systemic viral diseases, including, but not limited to, AIDS, influenza, the common cold, or encephalitis.

Representative infections that can be treated, include but are not limited to infections cause by microoganisms including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium,* Cytophaga, Deinococcus, *Escherichia, Francisella, Halobacterium, Heliobacter, Haemophilus, Hemophilus influenza* type B (HIB), *Histoplasma, Hyphomicrobium, Legionella, Leishmania, Leptspirosis, Listeria,* Meningococcus A, B and C, *Methanobacterium, Micrococcus, Myobacterium, Mycoplasma, Myxococcus, Neisseria, Nitrobacter,* Oscillatoria, Prochloron, *Proteus, Pseudomonas, Phodospirillum, Rickettsia, Salmonella, Shigella,* Spirillum, Spirochaeta, *Staphylococcus, Streptococcus, Streptomyces, Sulfolobus, Thermoplasma, Thiobacillus,* and *Treponema, Vibrio, Yersinia, Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Plasmodium vivax, Trypanosoma brucei, Entamoeba histolytica, Toxoplasma gondii, Trichomonas vaginalis* and *Schistosoma mansoni.*

In some embodiments, the type of disease to be treated or prevented is a chronic infectious disease caused by a bacterium, virus, protozoan, helminth, or other microbial pathogen that enters intracellularly and is attacked, e.g., by cytotoxic T lymphocytes.

In some embodiments, infections to be treated are chronic infections cause by a hepatitis virus, a human immunodeficiency virus (HIV), a human T-lymphotrophic virus (HTLV), a herpes virus, an Epstein-Barr virus, or a human papilloma virus.

Combination Therapies

In some embodiments, the albumin binding peptide conjugates of the disclosure are administered in combination with one or more additional therapeutic agents. The agents can be administered in the same pharmaceutical composition as the albumin binding peptide conjugate or the albumin binding peptide conjugate and the additional therapeutic agent can be administered in separate pharmaceutical compositions.

In some embodiments, the albumin binding peptide conjugate is administered in combination with a conventional therapeutic agent used for treatment of the disease or condition being treated. Conventional therapeutics agents are known in the art and can be determined by one of skill in the art based on the disease or disorder to be treated. For example, if the disease or condition is cancer, the albumin binding peptide conjugate can be co-administered with a chemotherapeutic drug; or if the disease or condition is a bacterial infection, the albumin biding peptide conjugate can be co-administered with an antibiotic. Other examples of therapeutic agents that may be co-administered with the albumin binding peptide conjugate include anti-tumor antibodies and checkpoint inhibitors.

Kits

A kit can include an albumin binding peptide (ABP) conjugate as disclosed herein, and instructions for use. The kits may comprise, in a suitable container, an albumin binding peptide conjugate, one or more controls, and various buffers, reagents, enzymes and other standard ingredients well known in the art.

The container can include at least one vial, well, test tube, flask, bottle, syringe, or other container means, into which an albumin binding peptide conjugate may be placed, and in some instances, suitably aliquoted. Where an additional component is provided, the kit can contain additional containers into which this component may be placed. The kits can also include a means for containing an albumin binding peptide conjugate, and any other reagent containers in close confinement for commercial sale. Such containers may include injection or blow-molded plastic containers into which the desired vials are retained. Containers and/or kits can include labeling with instructions for use and/or warnings.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al, Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pa.: Mack Publishing Company, 1990); Carey and Sundberg Advanced Organic Chemistry $3^{rd}$ Ed. (Plenum Press) Vols A and B (1992).

Example 1

Exemplary ABP-Antigen Constructs

The present disclosure provides evidence that albumin binding peptides may be used to enhance the antigenicity of peptide vaccines. Albumin binding peptides remain largely unexplored in the context of vaccinology. They have previously been used to extend the pharmacokinetics of protein therapeutics in several preclinical studies. The present disclosure provides the novel discovery that albumin binding peptides may be used in the preparation of peptide vaccines. To explore whether ABPs covalently linked to peptide antigens could direct these antigens to the lymphatic system exemplary ABP-antigen constructs were designed, synthesized, purified, and characterized.

Various embodiments of the ABP-antigen constructs of the disclosure are shown in FIG. 1.

ABP-PEG2k-EGP long has the configuration: Albumin binding peptide (cyclized DICLPRWGCLW (SEQ ID NO: 9)) operably coupled via a PEG2k linker to an EGP long peptide (AVGALEGPRNQDWLGVPRQL (SEQ ID NO: 41)).

ABP-G4S-EGP long (SEQ ID NO: 43) has the configuration: Albumin binding peptide (cyclized DICLPRWGCLW (SEQ ID NO: 9)) operably coupled via a Gly$_4$Ser linker (SEQ ID NO: 42) to an EGP long peptide (AVGALEGPRNQDWLGVPRQL (SEQ ID NO: 41)).

Example 2

ABP-Antigen Construct Synthesis and Purification

Figure 2:
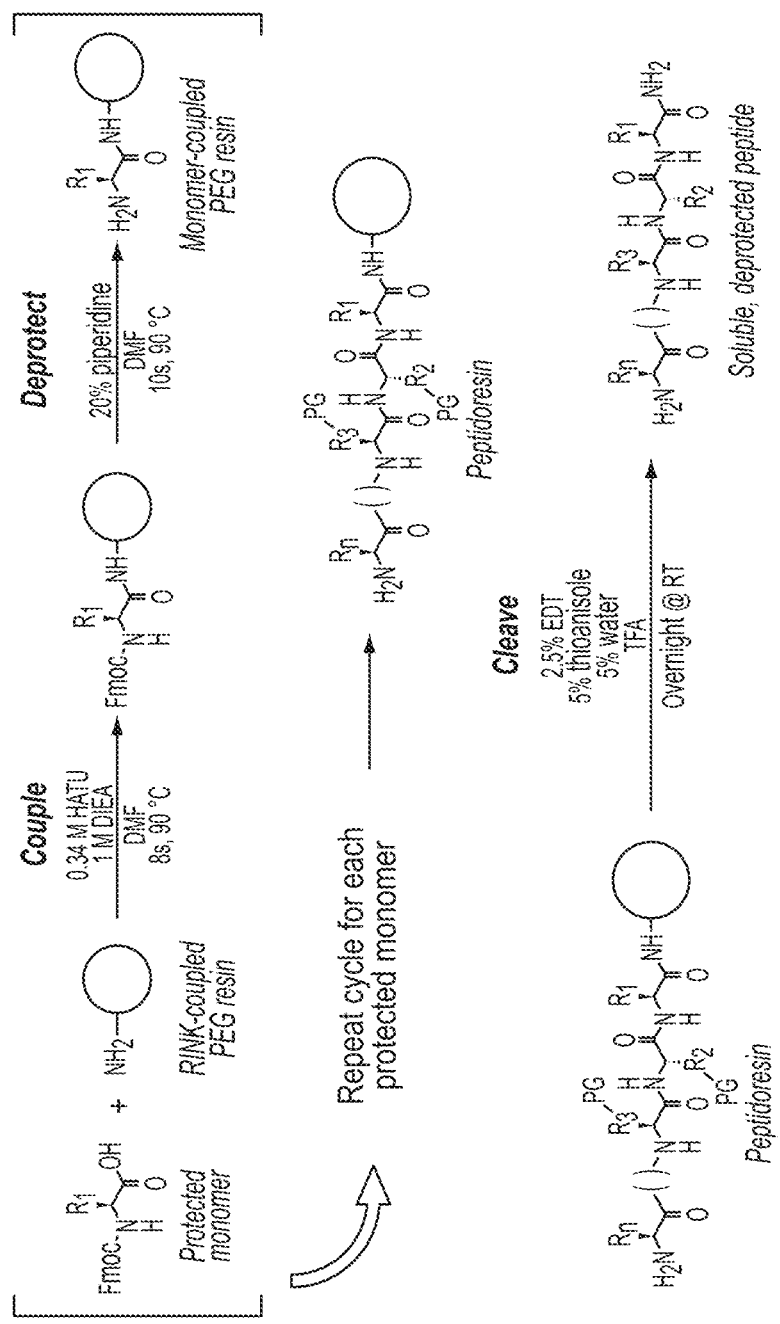
FIG. 2 is a schematic depicting the synthesis and purification of albumin binding peptide vaccines. Constructs were synthesized as a single unit via automated solid-phase peptide synthesis. Constructs were then purified via reverse-phase HPLC and isolated in mg quantities.

ABP-antigen constructs were synthesized as a single unit via automated solid phase peptide synthesis. Equal volumes of a protected amino acid monomer (0.4 M in DMF, Chem Impex) and HATU (1-[Bis(dimethylamino)methylene]-1H-1,2,3-triazolo[4,5-b]pyridinium 3-oxid hexafluorophosphate, Chem Impex) or PyAOP ((7-Azabenzotriazol-1-yloxy)tripyrrolidinophosphonium hexafluorophosphate, P3Bio) (0.34 M in DMF) were combined with diisopropylethylamine (neat, final concentration 1 M; Sigma) at 90° C. to form an active ester and coupled onto RINK-amide PEG (PCS Biomatrix) resin in flow at 90° C. After a DMF wash, the N-terminus of the coupled monomer was deprotected with piperidine (final concentration 1 M in DMF; Sigma), the peptiodresin was washed with DMF, and the cycle was repeated. These iterative coupling reactions (<1 min each) were performed in by an automated synthesizer as described (Mijalis, A. J. et al. A fully automated flow-based approach for accelerated peptide synthesis. *Nat Chem Biol advance online publication,* doi:10.1038/nchembio.2318 (2017)) to yield the ABP-antigen constructs. The PEG2000 linker (Creative PEGworks), which was purchased with protected amine and carboxylic acid groups at opposite termini, was coupled in a similar manner manually in batch at RT onto peptidoresin containing automatically synthesized antigen peptide; the resin was then transferred back to the automated synthesizer to complete the construct. The crude peptides were cleaved overnight at RT (by volume, 82.5% trifluoroacetic acid, 5% water, 5% thioanisole, 5% phenol, and 2.5% ethane dithiol; each from Sigma), triturated, and purified via reverse-phase HPLC. (FIGS. 1 and 2).

Example 3

Cyclization of ABP Moieties and Characterization of ABP-Antigen Constructs

Figure 3:
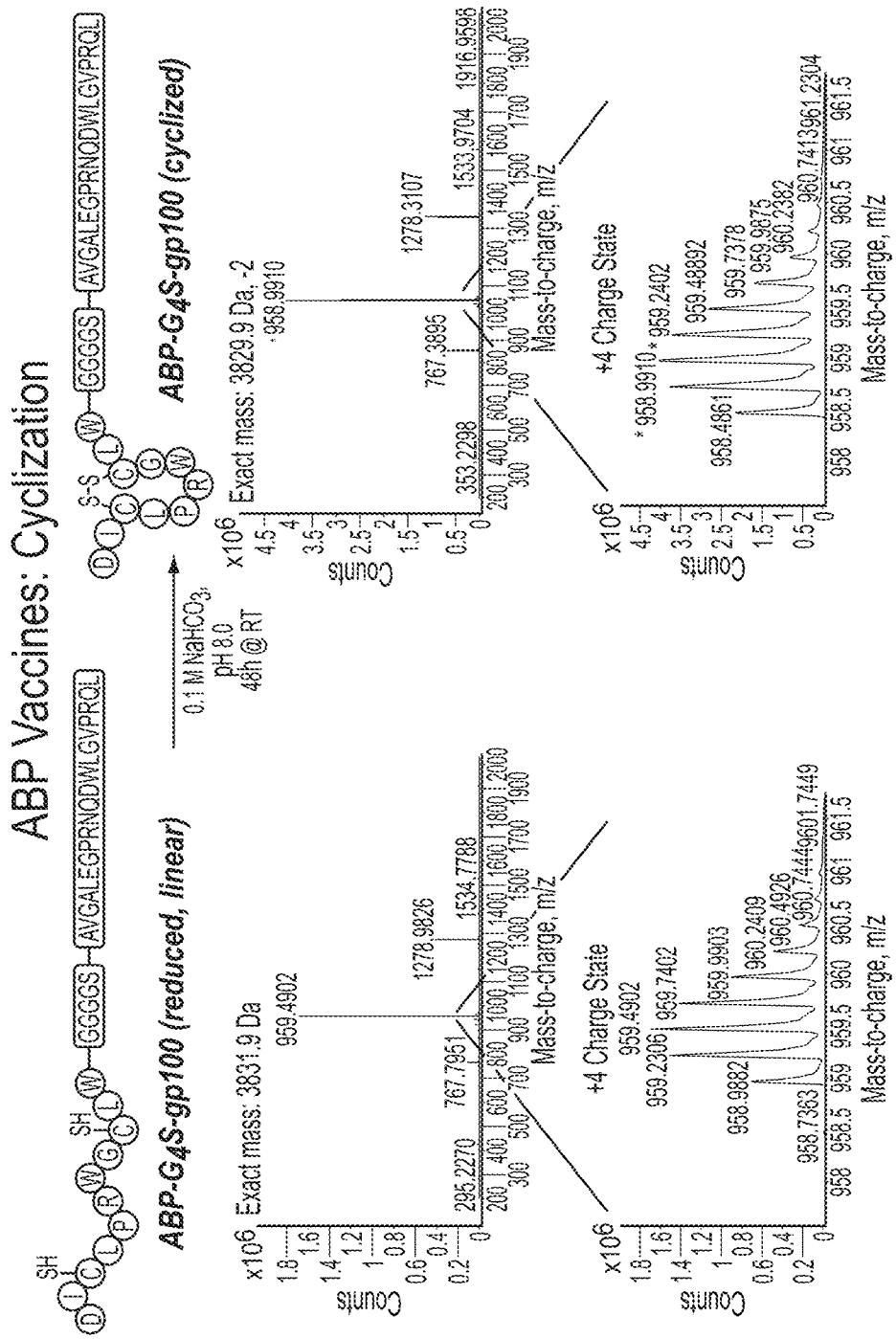
FIG. 3 is a schematic depicting the cyclization of albumin binding peptide vaccines (SEQ ID NO: 43). Constructs were cyclized by enabling spontaneous disulfide formation. Buffer was removed via solid-phase extraction.
Figure 4:
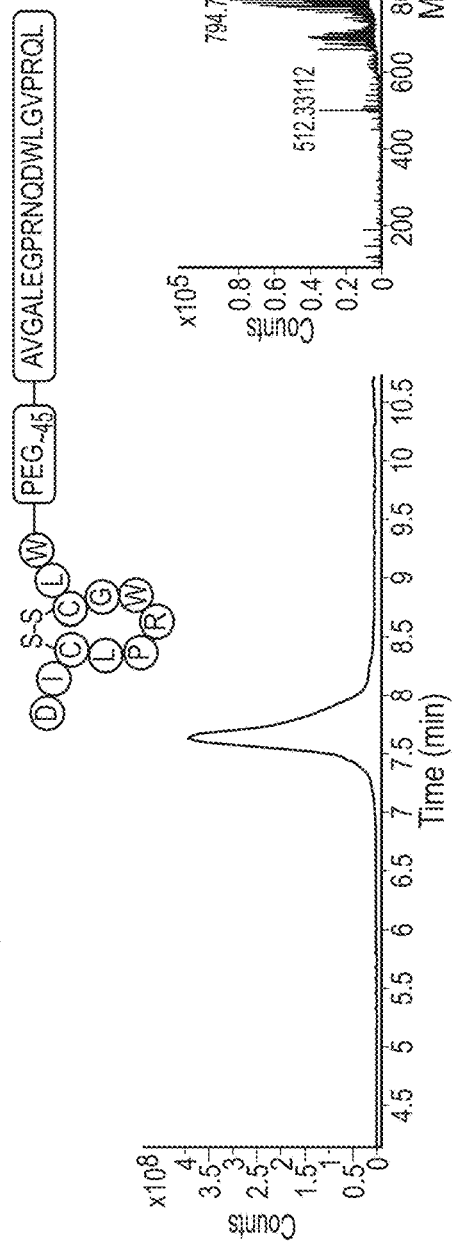
FIG. 4 depicts LC-MS analysis and characterization of the albumin binding peptide vaccines as depicted in FIG. 1 (SEQ ID NO: 9 operably coupled via a PEG2K linker to SEQ ID NO: 41 and SEQ ID NO: 9 operably coupled via a Gly$_4$Ser linker (SEQ ID NO: 42) to SEQ ID NO: 41).
Figure 4:
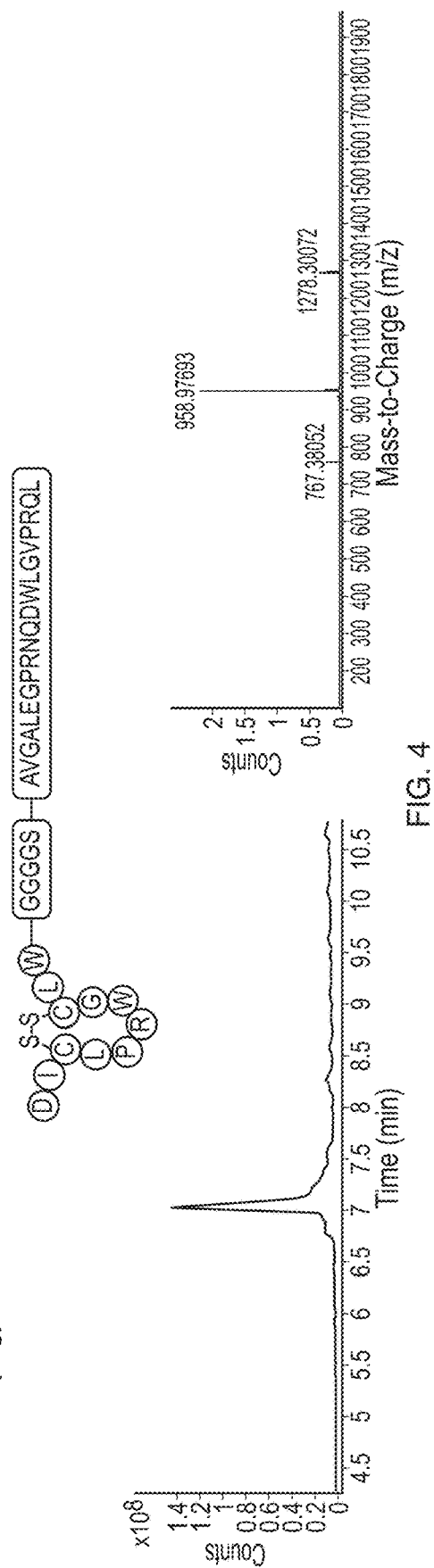

The ABP moieties were cyclized by incubating the purified constructs (0.1 mg/mL) in 0.1 M NaHCO$_3$(Sigma), pH 8.0 for 24 h to facilitate disulfide formation. The cyclized constructs were desalted via solid phase extraction and analyzed via LC-MS to verify identity and purity. (FIGS. 3 and 4).

Example 4

Immunization with ABP-Antigen Constructs

To test whether these albumin-binding peptides could enhance vaccination, a model melanoma antigen called gp100 was utilized. Vaccination against gp100 has shown significant preclinical activity (van Stipdonk, M. J. B. et al. Design of agonistic altered peptides for the robust induction of CTL directed towards H-2Db in complex with the melanoma-associated epitope gp100. *Cancer research* 69, 7784-7792, doi:10.1158/0008-5472.CAN-09-1724 (2009)) and has also been used clinically (Schwartzentruber, D. J. et al. gp100 Peptide Vaccine and Interleukin-2 in Patients with Advanced Melanoma. *New England Journal of Medicine* 364, 2119-2127, doi:10.1056/NEJMoa1012863 (2011)). An altered peptide ligand form of gp100 called EGP (sequence (SEQ ID NO: 41)
AVGALEGPRNQDWLGVPRQL, H2-D$^b$ epitope underlined) was shown to have enhanced affinity for MHC over the native form (called EGS) (van Stipdonk, M. J. B. et al. Design of agonistic altered peptides for the robust induction of CTL directed towards H-2Db in complex with the melanoma-associated epitope gp100. *Cancer research* 69, 7784-7792, doi:10.1158/0008-5472.CAN-09-1724 (2009)). This antigen was used to test in vivo for immunization.

Figure 5:
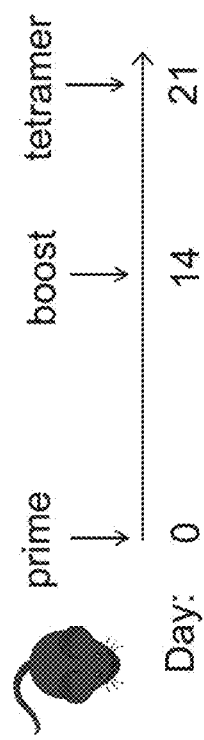
FIG. 5 is a schematic depicting the immunization regiment of the albumin binding peptide vaccines. Mice were primed on day 0, boosted on day 14, and tetramer staining was performed on day 21 to assess T cell priming in peripheral blood.
Figure 6:
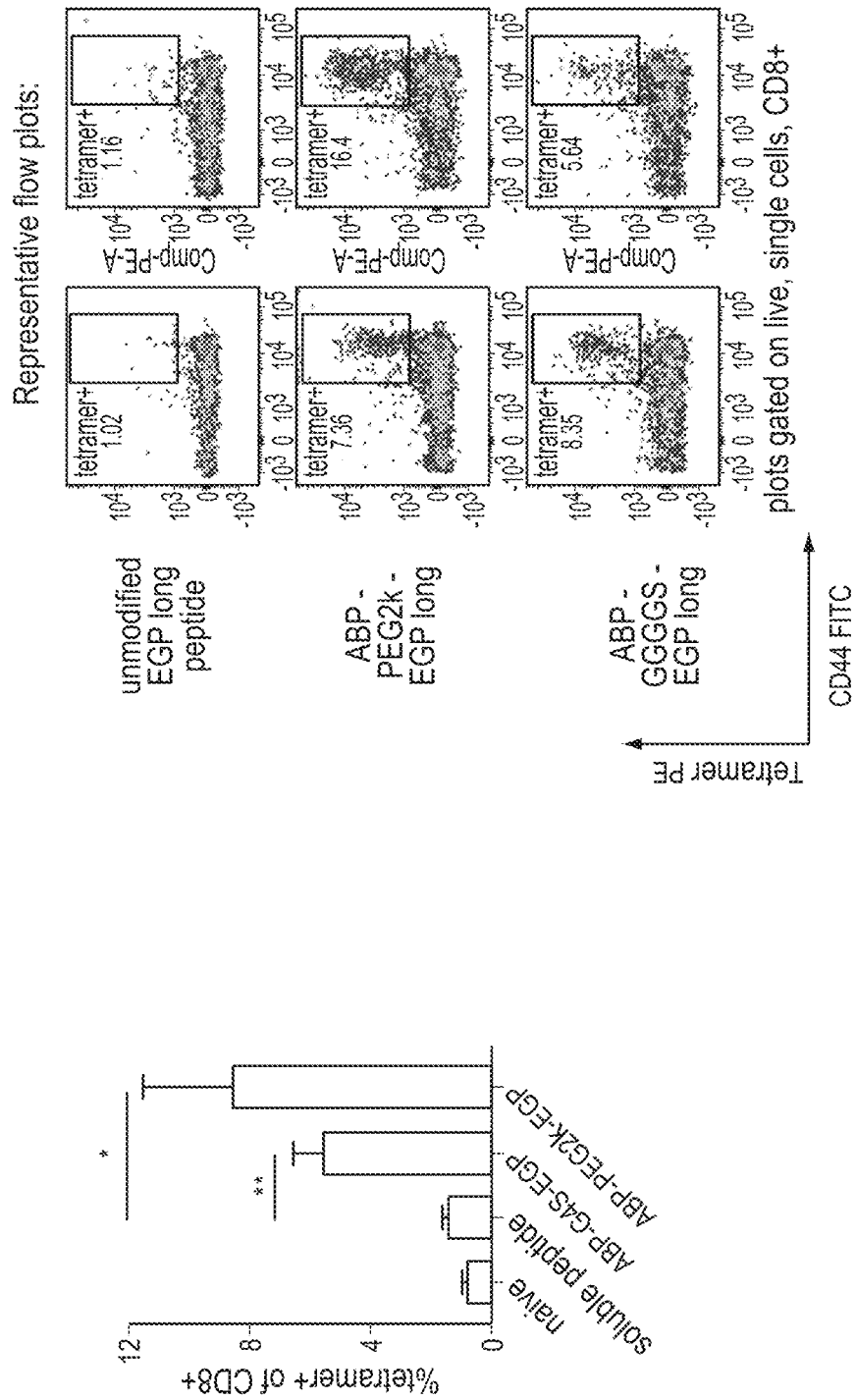
FIG. 6 graphically depicts the albumin binding peptide vaccine immunization results. The graph on the left depicts percentage CD44$^{hi}$ tetramer+ of total live CD8+ T cells. The graphs on the right depict representative flow plots for unmodified EGP long peptide, the ABP-PEG2K-EGP long construct, and the ABP-GGGS-EGP long construct.

To test the immunogenicity of ABP-modified peptides, C57BL6/J mice (Jackson Laboratories) were immunized with 5 nmol either ABP-G$_4$S-EGP, ABP-PEG$_{2000}$-EGP, or unmodified EGP peptide. Vaccines were formulated with 25 ug c-di-GMP (Invivogen) for adjuvant in 100 uL total volume (with sterile saline as diluent). Mice were primed on day 0, boosted on day 14, and tetramer staining was performed on day 21 to assess T cell priming in peripheral blood. (FIG. 5). Briefly, blood was isolated retro-orbitally, subjected to lysis to remove red blood cells, and incubated with tetramer (H-2Db gp100, MBL) at room temperature for 30 minutes, followed by surface staining for CD8 and CD44. DAPI was included as a viability marker, and cells were run on the LSR Fortessa (BD Biosciences). Responses were quantified as the percentage $CD44^{hi}$ tetramer+ of total live CD8+ T cells. The response to unmodified peptide was 1.45%, which was not statistically different from background in unimmunized mice, at 0.82%. The ABP-$G_4$S-EGP construct primed a mean response of 5.56%, or approximately 4-fold higher responses than unmodified peptide. The ABP-PEG2000-EGP construct primed a response of 8.58%, or approximately 6-fold higher than unmodified peptide. (FIG. 6).

In summary, the addition of an albumin-binding peptide linked through either a $G_4$S or PEG2000 spacer to a peptide antigen showed enhancement in T cell priming relative to unmodified peptide for a clinically relevant tumor sequence. This provides evidence that the ABP-antigen constructs may be a versatile platform for enhancing immunogenicity of poorly immunogenic peptides.

TABLE 1

| SEQ ID NO. | DESCRIPTION | SEQUENCE |
|---|---|---|
| 1 | Albumin binding peptide | $(Xaa)_x$-Xaa-Xaa-Cys-Xaa-Xaa-Xaa-Xaa-Xaa-Cys-Xaa-Xaa-$(Xaa)_z$ |
| 2 | Albumin binding peptide | $(Xaa)_x$-Phe-Cys-Xaa-Asp-Trp-Pro-Xaa-Xaa-Xaa-Ser-Cys-$(Xaa)_z$ |
| 3 | Albumin binding peptide | $(Xaa)_x$-Val-Cys-Tyr-Xaa-Xaa-Xaa-Ile-Cys-Phe-$(Xaa)_z$ |
| 4 | Albumin binding peptide | $(Xaa)_x$-Cys-Tyr-Xaa1-Pro-Gly-Xaa-Cys-$(Xaa)_z$ |
| 5 | Albumin binding peptide | $(Xaa)_x$-Asp-Xaa-Cys-Leu-Pro-Xaa-Trp-Gly-Cys-Leu-Trp-$(Xaa)_z$ |
| 6 | Albumin binding peptide | $(Xaa)_x$-Trp-Cys-Asp-Xaa-Xaa-Leu-Xaa-Ala-Xaa-Asp-Leu-Cys-$(Xaa)_z$ |
| 7 | Albumin binding peptide | $(Xaa)_x$-Asp-Leu-Val-Xaa-Leu-Gly-Leu-Glu-Cys-Trp-$(Xaa)_z$ |
| 8 | Albumin binding peptide | DLCLRDWGCLW |
| 9 | Albumin binding peptide | DICLPRWGCLW |
| 10 | Albumin binding peptide | MEDICLPRWGCLWGD |
| 11 | Albumin binding peptide | QRLMEDICLPRWGCLWEDDE |
| 12 | Albumin binding peptide | QGLIGDICLPRWGCLWGRSV |
| 13 | Albumin binding peptide | QGLIGDICLPRWGCLWGRSVK |
| 14 | Albumin binding peptide | EDICLPRWGCLWEDD |
| 15 | Albumin binding peptide | RLMEDICLPRWGCLWEDD |
| 16 | Albumin binding peptide | MEDICLPRWGCLWEDD |
| 17 | Albumin binding peptide | MEDICLPRWGCLWED |
| 18 | Albumin binding peptide | RLMEDICLARWGCLWEDD |
| 19 | Albumin binding peptide | EVRSFCTRWPAEKSCKPLRG |
| 20 | Albumin binding peptide | RAPESFVCYWETICFERSEQ |
| 21 | Albumin binding peptide | EMCYFPGICWM |
| 22 | Albumin binding peptide | $X_x$ D X C L P X W G C L W $X_z$ |
| 23 | Albumin binding peptide | $X_x$ F C X D W P X X X S C $X_z$ |
| 24 | Albumin binding peptide | $X_x$ V C Y X X X I C F $X_z$ |
| 25 | Albumin binding peptide | $X_x$ C Y $X_1$ P G X C X $X_z$ |
| 26 | Albumin binding peptide | DLCLRDWGCLW |
| 27 | Albumin binding peptide | DICLPRWGCLW |
| 28 | Albumin binding peptide | MEDICLPRWGCLWED |

TABLE 1-continued

| SEQ ID NO. | DESCRIPTION | SEQUENCE |
|---|---|---|
| 29 | Albumin binding peptide | QRLMEDICLPRWGCLWEDDF |
| 30 | Albumin binding peptide | QGLIGDICLPRWGCLWGDSV |
| 31 | Albumin binding peptide | QGLIGDICLPRWGCLWGDSVK |
| 32 | Albumin binding peptide | EDICLPRWGCLWEDD |
| 33 | Albumin binding peptide | RLMEDICLPRWGCLWEDD |
| 34 | Albumin binding peptide | MEDICLPRWGCLWEDD |
| 35 | Albumin binding peptide | MEDICLPRWGCLWED |
| 36 | Albumin binding peptide | RLMEDICLARWGCLWEDD |
| 37 | Albumin binding peptide | QRLMEDICLPRWGCLWEDDF |
| 38 | linker | LEA(EAAAK)$_4$ALEA(EAAAK)$_4$ALE |
| 39 | linker | GGSG |
| 40 | linker | GSAT |
| 41 | EGP long peptide | AVGALEGPRNQDWLGVPRQL |
| 42 | linker | GGGGS |
| 43 | ABP-G4S-EGP long | DICLPRWGCLWGGGGSAVGALEGPRNQDWLGVPRQL |

REFERENCES

Hacohen, N., Fritsch, E. F., Carter, T. A., Lander, E. S. & Wu, C. J. Getting personal with neoantigen-based therapeutic cancer vaccines. *Cancer Immunol Res* 1, 11-15, doi:10.1158/2326-6066.CIR-13-0022 (2013).

Melief, C. J. M. & van der Burg, S. H. Immunotherapy of established (pre)malignant disease by synthetic long peptide vaccines. *Nat Rev Cancer* 8, 351-360 (2008).

Liu, H. et al. Structure-based programming of lymph-node targeting in molecular vaccines. *Nature* 507, 519-522, doi:10.1038/nature12978 (2014).

Lindner, V. & Heinle, H. Binding properties of circulating evans blue in rabbits as determined by disc electrophoresis. *Atherosclerosis* 43, 417-422, (1982).

Dennis, M. S. et al. Albumin Binding as a General Strategy for Improving the Pharmacokinetics of Proteins. *Journal of Biological Chemistry* 277, 35035-35043 (2002).

Levy, O. E. et al. Novel Exenatide Analogs with Peptidic Albumin Binding Domains: Potent Anti-Diabetic Agents with Extended Duration of Action. *PLoS ONE* 9, e87704, doi:10.1371/journal.pone.0087704 (2014).

Mijalis, A. J. et al. A fully automated flow-based approach for accelerated peptide synthesis. *Nat Chem Biol advance online publication, doi:*10.1038/nchembio.2318 (2017).

van Stipdonk, M. J. B. et al. Design of agonistic altered peptides for the robust induction of CTL directed towards H-2Db in complex with the melanoma-associated epitope gp100. *Cancer research* 69, 7784-7792, doi:10.1158/0008-5472.CAN-09-1724 (2009).

Schwartzentruber, D. J. et al. gp100 Peptide Vaccine and Interleukin-2 in Patients with Advanced Melanoma. *New England Journal of Medicine* 364, 2119-2127, doi: 10.1056/NEJMoa1012863 (2011).

Davies-Venn, C. A., et al. Albumin-Binding domain Conjugate for Near-Infrared Fluorescence Lymphatic Imaging. *Molecular Imaging and Biology* 14: 301-314, doi: 10.1007/s11307-011-0499-x (2012).

Ma, Y. et al. A novel recombinant slow-release TNF a-derived peptide effectively inhibits tumor growth and angiogenesis. *Scientific Reports* 5:13595, doi: 10.1038/srep13595 (2015).

EQUIVALENTS

Those skilled in the art will recognize or be able to ascertain, using no more than routine experimentation, many equivalents of the specific embodiments described herein. Such equivalents are intended to be encompassed by the following claims.

We claim:

1. A conjugate for priming an endogenous immune response comprising:
   (a) an albumin binding peptide; and
   (b) an immunomodulatory molecule, wherein the immunomodulatory molecule is a peptide antigen or an immunostimulatory oligonucleotide,
   and wherein the albumin binding peptide is operatively coupled to the immunomodulatory molecule with or without a linker domain, thereby providing a conjugate for priming an endogenous immune response.

2. The conjugate of claim 1, wherein the albumin binding peptide is covalently linked to the immunomodulatory molecule, or the albumin binding peptide is operatively coupled to the immunomodulatory molecule via a linker domain.

3. The conjugate of claim 2, wherein the linker domain comprises a Gly-Ser linker or a polyethylene glycol (PEG) linker.

4. The conjugate of claim 3, wherein the Gly-Ser linker is a $(Gly_4Ser)_n$ (SEQ ID NO: 44) linker, and wherein n is 1-6.

5. The conjugate of claim 3, wherein the PEG linker is a $PEG_{2000}$ linker.

6. The conjugate of claim 1, wherein the peptide antigen is a cancer antigen or a melanoma antigen.

7. The conjugate of claim 1, wherein the immunostimulatory oligonucleotide is CpG DNA.

8. The conjugate of claim 1, wherein the albumin binding peptide comprises the amino acid sequence DICL-PRWGCLW (SEQ ID NO: 9).

9. A vaccine comprising the conjugate of claim 1 and a pharmaceutically acceptable carrier or excipient.

10. The vaccine of claim 9 further comprising an adjuvant.

11. A composition for directing immunomodulatory molecules to the lymphatic system, wherein the composition comprises a conjugate comprising:
    (a) an albumin binding peptide; and
    (b) an immunomodulatory molecule,
    wherein the immunomodulatory molecule is a peptide antigen or an immunostimulatory oligonucleotide, and wherein the albumin binding peptide is operatively coupled to the immunomodulatory molecule with or without a linker domain.

12. The composition of claim 11, wherein the conjugate exhibits increased accumulation in the lymph node when administered to the subject in vivo compared to administration of the antigen alone.

13. An immunogenic composition comprising the conjugate of claim 1.

14. An immunogenic composition comprising the vaccine of claim 9.

15. A nucleic acid molecule encoding the conjugate according to claim 1.

16. A recombinant expression vector comprising a nucleic acid molecule according to claim 15.

17. A host cell transformed with the recombinant expression vector according to claim 16.

18. The composition of claim 11, wherein the albumin binding peptide is covalently linked to the immunomodulatory molecule, or the albumin binding peptide is operatively coupled to the immunomodulatory molecule via a linker domain.

19. The composition of claim 18, wherein the linker domain comprises a Gly-Ser linker or a polyethylene glycol (PEG) linker.

20. The composition of claim 19, wherein the Gly-Ser linker is a $(Gly_4Ser)_n$ (SEQ ID NO: 44) linker.

21. The composition of claim 19, wherein the PEG linker is a $PEG_{2000}$ linker.

22. The composition of claim 11, wherein the peptide antigen is a cancer antigen or a melanoma antigen.

23. The composition of claim 11, wherein the immunostimulatory oligonucleotide is CpG DNA.

24. The composition of claim 11, wherein the albumin binding peptide comprises the amino acid sequence DICL-PRWGCLW (SEQ ID NO: 9).

* * * * *